US011992008B2

United States Patent
Asirvatham

(10) Patent No.: US 11,992,008 B2
(45) Date of Patent: May 28, 2024

(54) SURFACTANTS FOR AGRICULTURAL PRODUCTS

(71) Applicant: AdvanSix Resins & Chemicals LLC, Parsippany, NJ (US)

(72) Inventor: Edward Asirvatham, Chatham, NJ (US)

(73) Assignee: AdvanSix Resins & Chemicals LLC, Parsippany, NJ (US)

( * ) Notice: Subject to any disclaimer, the term of this patent is extended or adjusted under 35 U.S.C. 154(b) by 76 days.

(21) Appl. No.: 17/196,874

(22) Filed: Mar. 9, 2021

(65) Prior Publication Data

US 2021/0289776 A1    Sep. 23, 2021

Related U.S. Application Data

(60) Provisional application No. 62/988,203, filed on Mar. 11, 2020.

(51) Int. Cl.
*A01N 25/30* (2006.01)
*A01N 37/44* (2006.01)
*A01N 41/08* (2006.01)

(52) U.S. Cl.
CPC ............ *A01N 25/30* (2013.01); *A01N 37/44* (2013.01); *A01N 41/08* (2013.01)

(58) Field of Classification Search
CPC ........ A01N 25/30; A01N 37/44; A01N 41/08; C07C 291/04; C07C 229/10; C07C 229/08; C07C 309/14
See application file for complete search history.

(56) References Cited

U.S. PATENT DOCUMENTS

| | | | |
|---|---|---|---|
| 3,213,500 | A | 10/1965 | Thompson |
| 3,704,486 | A | 12/1972 | Blacklock |
| 4,276,460 | A | 6/1981 | Haesly et al. |
| 4,297,769 | A | 11/1981 | Coules |
| 4,502,193 | A | 3/1985 | Harmon et al. |
| 4,664,458 | A | 5/1987 | Worth |
| 5,060,100 | A | 10/1991 | Mihara et al. |
| 5,580,203 | A | 12/1996 | Read et al. |
| 5,706,559 | A | 1/1998 | Oliver et al. |
| 5,798,095 | A | 8/1998 | Racky |
| 5,958,894 | A | 9/1999 | Heath et al. |

(Continued)

FOREIGN PATENT DOCUMENTS

| | | |
|---|---|---|
| CN | 105802600 A | 7/2016 |
| CN | 108024935 A | 5/2018 |

(Continued)

OTHER PUBLICATIONS

Focus Technology Company, Daily Chemical Grade Antifreeze Thickener Hydroxypropyl Methylcellulose HPMC, Accessed 2023, pp. 1-5. (Year: 2023).*

(Continued)

*Primary Examiner* — Trevor Love
(74) *Attorney, Agent, or Firm* — Faegre Drinker Biddle & Reath LLP

(57) ABSTRACT

Agricultural products, such as pesticides, plant growth regulators, fungicides, herbicides, and insecticides, may be formulated to include one or more surfactants, from one or more surfactant classes, such as derivatives of amino acids that have surface-active properties.

17 Claims, 10 Drawing Sheets

(56) References Cited

U.S. PATENT DOCUMENTS

| | | | |
|---|---|---|---|
| 5,972,323 | A | 10/1999 | Lang et al. |
| 6,114,757 | A | 9/2000 | Delprete |
| 6,304,986 | B1 | 10/2001 | Ma et al. |
| 6,501,030 | B1 | 12/2002 | Parizi et al. |
| 6,702,592 | B1 | 3/2004 | Harden et al. |
| 7,646,556 | B1 | 1/2010 | Kose et al. |
| 7,653,847 | B1 | 1/2010 | Liikanen et al. |
| 7,768,736 | B2 | 8/2010 | Belmont et al. |
| 8,599,507 | B2 | 12/2013 | Sanvido et al. |
| 8,964,320 | B1 | 2/2015 | Hu et al. |
| 9,142,246 | B1 | 9/2015 | Trantham et al. |
| 9,484,059 | B2 | 11/2016 | Lim et al. |
| 9,552,846 | B1 | 1/2017 | Lim |
| 2003/0081357 | A1 | 5/2003 | Hong et al. |
| 2008/0259100 | A1 | 10/2008 | Rengaswamy et al. |
| 2013/0336903 | A1 | 12/2013 | Fernandez et al. |
| 2017/0079898 | A1 | 3/2017 | Fevola et al. |
| 2021/0229053 | A1 | 7/2021 | Asirvatham et al. |
| 2021/0230100 | A1 | 7/2021 | Asirvatham et al. |
| 2021/0230106 | A1 | 7/2021 | Asirvatham et al. |
| 2021/0230107 | A1 | 7/2021 | Asirvatham et al. |
| 2021/0230108 | A1 | 7/2021 | Asirvatham et al. |
| 2021/0283030 | A1 | 9/2021 | Asirvatham |
| 2021/0284896 | A1 | 9/2021 | Asirvatham |
| 2021/0284936 | A1 | 9/2021 | Asirvatham |
| 2021/0290765 | A1 | 9/2021 | Asirvatham |
| 2021/0292583 | A1 | 9/2021 | Asirvatham |
| 2021/0292647 | A1 | 9/2021 | Asirvatham |

FOREIGN PATENT DOCUMENTS

| | | | |
|---|---|---|---|
| DE | 3939746 | A1 | 6/1991 |
| DE | 29622184 | U1 | 2/1997 |
| EP | 0638236 | A1 | 2/1995 |
| EP | 0826661 | A2 | 3/1998 |
| GB | 2204740 | A | 11/1988 |
| GB | 2311033 | A | 9/1997 |
| JP | 49-082624 | A | 8/1974 |
| JP | 61-278341 | A | 12/1986 |
| JP | 04-349284 | A | 12/1992 |
| JP | 08-007556 | A | 1/1996 |
| JP | 09-266021 | A | 10/1997 |
| JP | 11-233910 | A | 8/1999 |
| JP | 2006-294170 | A | 10/2006 |
| JP | 2017-195029 | A | 10/2017 |
| WO | 98/45233 | A2 | 10/1998 |
| WO | 03/68377 | A1 | 8/2003 |
| WO | 2012/061093 | A1 | 5/2012 |
| WO | 2017/012087 | A1 | 1/2017 |
| WO | 2017/048555 | A1 | 3/2017 |
| WO | 2017/199921 | A1 | 11/2017 |
| WO | 2018/115191 | A1 | 6/2018 |

OTHER PUBLICATIONS

International Search Report and Written Opinion received for PCT Patent Application No. PCT/US2021/014440, dated Apr. 30, 2021, 9 pages.

International Search Report and Written Opinion received for PCT Patent Application No. PCT/US2021/014444, dated Apr. 26, 2021, 12 pages.

International Search Report and Written Opinion received for PCT Patent Application No. PCT/US2021/014445, dated Apr. 26, 2021, 9 pages.

International Search Report and Written Opinion received for PCT Patent Application No. PCT/US2021/014447, dated Apr. 30, 2021, 9 pages.

International Search Report and Written Opinion received for PCT Patent Application No. PCT/US2021/014457, dated Apr. 30, 2021, 8 pages.

Novotny et al., "Transkarbams as transdermal permeation enhancers: effects of ester position and ammonium carbamate formation", Bioorganic & medicinal chemistry letters, vol. 20, No. 9, May 1, 2010, pp. 2726-2728.

Yasa et al., "Synthesis, characterization, antimicrobial and biofilm inhibitory activities of new N-oxide esters", Medicinal Chemistry Research, vol. 26, No. 8, Apr. 3, 2017, pp. 1689-1696.

Hrabálek et al., "Esters of omega-amino acids as flexible penetration enhancers", Pharmazie, vol. 49, No. 5, May 1994, pp. 325-328.

International Search Report and Written Opinion received for PCT Patent Application No. PCT/US2021/021565, dated Jun. 18, 2021, 13 pages.

International Search Report and Written Opinion received for PCT Patent Application No. PCT/US2021/021569, dated May 17, 2021, 9 pages.

International Search Report and Written Opinion received for PCT Patent Application No. PCT/US21/21571, dated Jul. 9, 2021, 9 pages.

International Search Report and Written Opinion received for PCT Patent Application No. PCT/US21/21574, dated Jul. 1, 2021, 10 pages.

International Search Report and Written Opinion received for PCT Patent Application No. PCT/US21/21595, dated Jul. 30, 2021, 15 pages.

International Search Report and Written Opinion received for PCT Patent Application No. PCT/US21/21596, dated Jun. 22, 2021, 10 pages.

International Search Report and Written Opinion received for PCT Patent Application No. PCT/US21/21597, dated Aug. 9, 2021, 11 pages.

Invitation to Pay Additional Fees received for PCT Patent Application No. PCT/US21/21595, dated Jun. 9, 2021, 9 pages.

Invitation to Pay Additional Fees received for PCT Patent Application No. PCT/US21/21597, dated Jun. 17, 2021, 7 pages.

Kerry P. Mahon et al: "Combinatorial Approach to Determine Functional Group Effects on Lipidoid-Mediated si RNA Delivery", Bioconjugate Chemistry, vol. 21, No. 8, Aug. 18, 2010 (Aug. 18, 2010), pp. 1448-1454.

* cited by examiner

SURFACTANTS FOR AGRICULTURAL PRODUCTS

CROSS-REFERENCE TO RELATED APPLICATION

This application claims priority to Provisional Application No. 62/988,203, filed Mar. 11, 2020, which is herein incorporated by reference in its entirety.

FIELD

The present disclosure pertains to surfactants for use in agricultural products. Such surfactants may include derivatives of amino acids wherein the derivatives have surface-active properties.

BACKGROUND

Surfactants (molecules with surface-active properties) are widely used in commercial agricultural formulations. These formulations may include a variety of active agricultural agents, such as pesticides, plant growth regulators, fungicides, herbicides, and insecticides. Many such active agricultural agents display limited water solubility or may be prone to crystallization. Precipitation of the active agricultural agent may result in a loss of efficiency. Should the active agent be concentrated in the precipitates, it is prevented from being evenly distributed when sprayed on a field. Thus, surfactants may be included in formulations to improve solubility, wetting, and spreadability of the active agent.

The surfactants may be uncharged, zwitterionic, cationic, or anionic. Although in principle any surfactant class (e.g., cationic, anionic, nonionic, amphoteric) is suitable, it is possible that a formulation may include a combination of two or more surfactants from two or more surfactant classes.

Often, surfactants are amphiphilic molecules with a relatively water-insoluble hydrophobic "tail" group and a relatively water-soluble hydrophilic "head" group. These compounds may adsorb at an interface, such as an interface between two liquids, a liquid and a gas, or a liquid and a solid. In systems comprising relatively polar and relatively non-polar components the hydrophobic tail preferentially interacts with the relatively non-polar component(s) while the hydrophilic head preferentially interacts with the relatively polar component(s). In the case of an interface between water and oil, the hydrophilic head group preferentially extends into the water, while the hydrophobic tail preferentially extends into the oil. When added to a water-gas interface, the hydrophilic head group preferentially extends into the water, while the hydrophobic tail preferentially extends into the gas. The presence of the surfactant disrupts at least some of the intermolecular interaction between the water molecules, replacing at least some of the interactions between water molecules with generally weaker interactions between at least some of the water molecules and the surfactant. This results in lowered surface tension and can also serve to stabilize the interface.

At sufficiently high concentrations, surfactants may form aggregates which serve to limit the exposure of the hydrophobic tail to the polar solvent. One such aggregate is a micelle. In a typical micelle the molecules are arranged in a sphere with the hydrophobic tails of the surfactant(s) preferentially located inside the sphere and the hydrophilic heads of the surfactant(s) preferentially located on the outside of the micelle where the heads preferentially interact with the more polar solvent. The effect that a given compound has on surface tension and the concentration at which it forms micelles may serve as defining characteristics for a surfactant.

SUMMARY

The present disclosure provides formulations of agricultural products, such as pesticides, plant growth regulators, fungicides, herbicides, and insecticides. These products may be formulated to include one or more surfactants from one or more surfactant classes disclosed herein. The surfactants may be used as emulsifiers, wetting agents, dispersants, and/or agents to improve spreadability. Additionally, surfactants may be used as adjuvants and agents to control spin drift.

The present disclosure provides surfactants for agricultural products in the form of derivatives of amino acids that have surface-active properties. The amino acids may be naturally occurring or synthetic amino acids, or they may be obtained via ring-opening reactions of molecules such as lactams, for instance caprolactam. The amino acids may be functionalized to form compounds with surface-active properties. Characteristically, these compounds may have low critical micelle concentrations (CMC) and/or the ability to reduce the surface tension of a liquid.

The present disclosure provides a formulation for a pesticide or plant growth regulator, comprising at least one surfactant of Formula I,

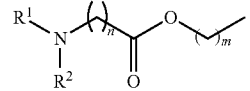

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide; a pesticide or plant growth regulator; and a water-insoluble solvent.

The present disclosure further provides a formulation for a fungicide, comprising at least one surfactant of Formula I,

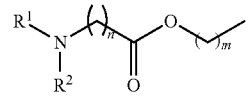

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide; an optional co-surfactant, and an optional carrier agent, such as a solvent or solid carrier.

The present disclosure also provides a formulation for an herbicide, comprising at least one surfactant of Formula I,

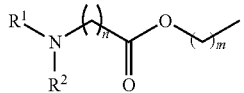

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide; one or more herbicides, a water-insoluble solvent, and water.

The present disclosure further provides a formulation for an insecticide, comprising at least one surfactant of Formula I,

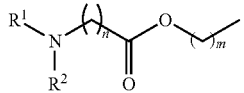

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide; an insecticide, an optional antifoaming agent, an optional antifreezing agent, and water.

The above mentioned and other features of the disclosure, and the manner of attaining them, will become more apparent and will be better understood by reference to the following description of embodiments taken in conjunction with the accompanying drawings.

DETAILED DESCRIPTION

Figure 1:
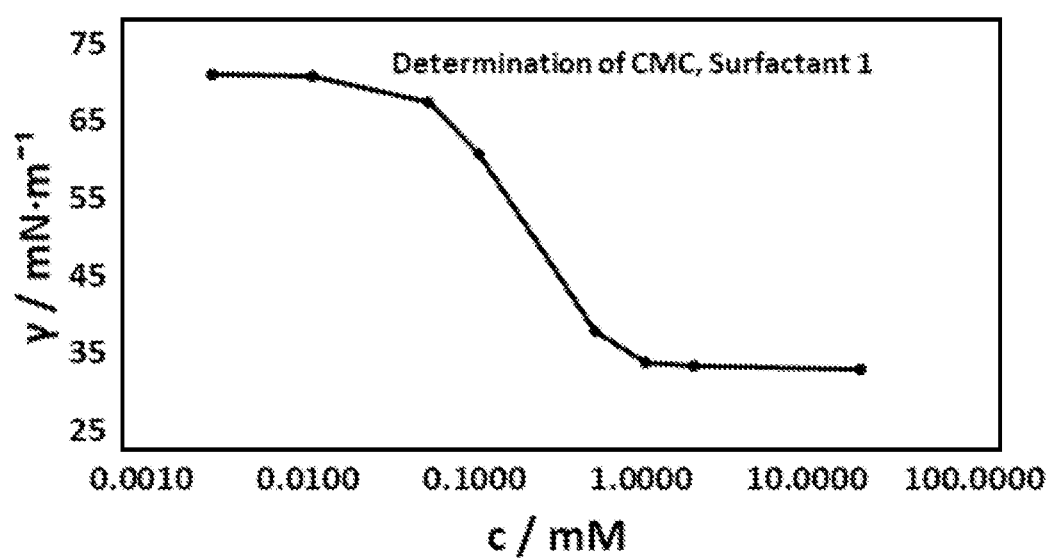
FIG. 1 shows a plot of surface tension versus concentration for Surfactant 1 measured at pH=7 as described in Example 1 b, wherein the Y axis depicts the surface tension ($\gamma$) in millinewtons per meter (mN/m) and the X axis depicts the concentration (c) in millimoles (mM).

As used herein, the phrase "within any range using these endpoints" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the word "alkyl" means any saturated carbon chain, which may be a straight or branched chain.

As used herein, the phrase "surface-active" means that the associated compound is able to lower the surface tension of the medium in which it is at least partially dissolved, and/or the interfacial tension with other phases, and, accordingly, may be at least partially adsorbed at the liquid/vapor and/or other interfaces. The term "surfactant" may be applied to such a compound.

With respect to the terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example. In the event it is determined that individuals having ordinary skill in the relevant arts would not readily ascertain values for such reasonably small differences, the terms "about" and "approximately" can be understood to mean plus or minus 10% of the stated value.

The present disclosure provides formulations of agricultural products, such as pesticides, plant growth regulators, fungicides, insecticides, and herbicides.

I. Pesticide and Plant Growth Regulator Formulations

Active agricultural agents such as pesticides have conventionally been provided to the end-user in different concentrated forms to be diluted in water or other suitable medium to a dilute ready-to-use formulation by the end-user. Such concentrated forms include solid formulations, e.g. powders, and liquid formulations. In many applications, liquid formulations are preferred as problems of dusting of toxic powders and slow dissolution in the diluent may be avoided.

The liquid concentrated formulations include so-called emulsion concentrates and soluble liquid concentrates. An emulsion concentrate comprises a pesticide, a water-insoluble solvent, and an emulsifier, and when added to the water, it spontaneously, or after mixing, forms an oil-in-water emulsion, the agricultural active primarily being present in the emulsion droplets. This type of concentrated formulation is especially suitable for agricultural actives that are water insoluble/have low water solubility, and where the recommended concentration in the ready-to-use formulation exceeds the solubility of the agricultural active.

The present disclosure provides a pesticide or plant growth regulator formulation with a high concentration of the agriculturally active agent, suitable for long term storage and delivery to the end user, who eventually will treat plants by contacting the plant with an agricultural formulation prepared from the concentrated pesticidal formulation described herein.

The pesticide formulations of the present disclosure may include an agriculturally active agent (a pesticide or a plant growth regulator), one or more surfactants or co-surfactants chosen from one or more surfactant classes, and a water-insoluble solvent.

1. Pesticide

The term "pesticide," as used herein, is well known in the art and is described at least by the Environmental Protection Agency (EPA), in the Federal Insecticide, Fungicide, and Rodenticide Act (FIFRA), in the Insecticides and Environmental Pesticide Control Subchapter (7 U.S.C. § 136(u)), in the Code of Federal Regulations (CFR) relating to the "Protection of Environment," and in the Regulations of the EPA in 40 CFR § 152.3. A pesticide is typically recognized in the art as a substance that is used for preventing, destroying, repelling, regulating, and/or mitigating any pest. A pest is an organism that is deleterious to man or the environment but does not include any internal parasite of living man or other living animal or any fungus, bacterium, virus, or other microorganism on or in living man or other living animals. Said differently, the terminology "pest" does not typically include any organism that infects or sickens humans or animals. In addition, the terminology "pesticide," as used herein, does not typically include any human or animal drugs or pharmaceuticals, any article that is a "new animal drug" as defined in the art, any liquid sterilant applied to a device used in the human body, and/or any products intended for use against fungi, bacteria, viruses, or other microorganisms in or on living man or living animal. Moreover, the pesticide of this disclosure does not typically include drugs or pharmaceuticals used to control diseases of humans or animals (such as livestock and pets).

As used herein, the term "plant growth regulator" refers to a compound, which through physiological action will accelerate or retard the rate of growth or rate of maturation or otherwise alter the behavior of ornamental or crop plants or the products thereof.

Pesticides and plant growth regulators especially contemplated for use in the present invention are organic compounds, preferably synthetic organic compounds. Suitable pesticides and plant growth regulators include triazoles, strobilurins, alkylenebis(dithiocarbamate) compounds, benzimidazoles, phenoxy carboxylic acids, benzoic acids, ureas, sulfonylureas, triazines, pyridine carboxylic acids, neonicotinides, amidines, organophosphates, and pyrethroids. The pesticide may have a water solubility of 1 g/L or less.

In a concentrated formulation of the present disclosure, the pesticide or plant growth regulator may be present in an amount of about 5 wt. % or greater, about 10 wt. % or greater, about 15 wt. % or greater, about 20 wt. % or greater, or about 25 wt. % or lower, about 30 wt. % or lower, about 35 wt. % or lower, about 40 wt. % or lower, or within any range using these endpoints, by weight of the composition.

2. Surfactant

The pesticide formulations of the present disclosure comprise one or more surfactants, also referred to as the surfactant system. The surfactant system is included to emulsify the composition, and/or to act as an adjuvant. The surfactant system comprises at least one surfactant, which may be an amphoteric surfactant, a zwitterionic surfactant, a cationic surfactant, a nonionic surfactant, and optionally at least one other surfactant, which may be an amphoteric surfactant, a zwitterionic surfactant, a cationic surfactant, a nonionic surfactant, or a combination thereof. Such surfactants should be physically and chemically compatible with the essential components described herein, or should not otherwise unduly impair product stability, aesthetics, or performance.

Suitable surfactants for use in the pesticide formulations of the present disclosure include one or more surfactants and/or co-surfactants of Formula I,

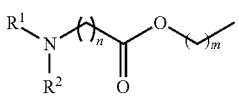

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide.

In particular, suitable surfactants or co-surfactants may include one or more of any of Surfactants 1-5 described herein.

The concentration of the surfactant system in the pesticide formulation may range from about 20 wt. % or greater, about 30 wt. % or greater, about 40 wt. % or greater, or about 50 wt. % or lower, about 60 wt. % or lower, about 70 wt. % or lower, or about 80 wt. % or lower, or within any range using these endpoints, by weight of the composition.

3. Water-Insoluble Solvent

The pesticide formulations of the present disclosure may include a water-insoluble solvent. A solvent is considered water-insoluble if its water solubility is about 10 g/L of water or less, about 5 g/L of water or less, about 1 g/L of water or less, or about 0.1 g/L or water or less at 20° C.

Suitable water-insoluble solvents may include aromatic solvents such as those sold under the tradename of Solvesso, and water-insoluble alcohols, such as linear or branched, aliphatic or aromatic, saturated or unsaturated alcohols with at least 6 carbon atoms.

4. Other additives

The pesticide formulation may include other additives such as additional surfactants, water, thickeners, deposition enhancers, drift control agents, salts, stabilizers, penetrants, spreading agents, wetting agents, building agents, extending agents, emulsifiers, dispersants, suspending agents, plant penetrants, translocators, oils, activators, foliar nutrients, compatibility agents, drift retardants, foam retardants, buffers, inverting agents, soil penetrants, stabilizing agents, UV filters, feeding stimulants, washing agents, sinking agents, binders, liquid carriers, dry carriers such as attapulgite, kaolinite, vermiculite, starch polymers, corn cob, and combinations thereof. The pesticide formulation may also include additional chemical compounds that are not pesticides, such as activators, anti-feedants, anti-fouling agents, attractant agents, chemosterilants, disinfectant agents, fumigant agents, pheromones, repellent agents, defoliants, desiccants, insect growth regulators, plant growth regulators, synergists, adjuvants, and combinations thereof.

These additives may be independently present in the pesticidal formulation in an amount of about 0 wt. % greater, about 5 wt. % or greater, about 10 wt. % or greater, about 15 wt. % or greater, or about 20 wt. % or lower, about 25 wt. % or lower, about 30 wt. % or lower, or within any range using these endpoints.

Additional surfactants, such as additional anionic, non-ionic, cationic, amphoteric, and zwitterionic surfactants, may present in the concentrated composition at a concentration of about 5 wt. % or greater, about 10 wt. % or greater, about 15 wt. % or greater, about 20 wt. % or greater, or about 25 wt. % or lower, about 30 wt. % or lower, about 35 wt. % or lower, about 40 wt. % or lower, or within any range using these endpoints, by weight of the composition.

Water may be present in the concentrated composition at a concentration of about 0 wt. % or greater, about 5 wt. % or greater, about 10 wt. % or greater, about 20 wt. % or greater, about 30 wt. % or greater, or about 35 wt. % or lower, about 45 wt. % or lower, about 55 wt. % or lower, about 65 wt. % or lower, or within any range using these endpoints, by weight of the composition.

Polymers may be included in the concentrated composition, as thickeners, deposition enhancers, or drift control agents. Suitable polymers may include polysaccharide ethers and synthetic polymers.

Water-soluble organic solvents, such as glycol ethers, such as butyl diglycol, N-formyl-morpholine, shorter aliphatic alcohols, propylene carbonate, etc. may be present in the pesticidal formulation at a weight ratio water-soluble organic solvent:water-insoluble organic solvent of at most 1:2.

5. Method of Making

The method includes the step of combining the surfactant system, the pesticide, and optionally the solvent. This step may also include adding any additives described above. The aforementioned components and compounds may be added in any order to one or more of each other and in any amount and in one or more individual steps, e.g. in whole or in parts.

6. Method of Use

The concentrated pesticidal formulation of the present disclosure may be in liquid form at room temperature and atmospheric pressure, with the agriculturally active ingredient solubilized therein.

The concentrated pesticidal formulation is intended to be mixed with an aqueous medium, typically tap water, before end use. The concentrated composition is added to a tank, before, simultaneously with or after, addition of the aqueous medium (water) to the tank. The concentrated pesticidal composition is therewith diluted to a suitable concentration of the agriculturally active.

The water content in the diluted pesticidal formulation of the present disclosure may be from about 75 wt. % or greater, about 90 wt. % or greater, about 99 wt. % or greater, or about 99.9 wt. % or greater, based on the total weight of the diluted composition, and will ultimately depend on the amount of water needed to dilute the agriculturally active ingredient in the concentrated pesticidal formulation of the present disclosure to the desired concentration in the ready-to-use composition.

When mixed with and diluted in the aqueous medium, the agriculturally active is evenly distributed in the aqueous medium, in the form of a solution or a fine emulsion and can be diluted substantially without any crystal growth occurring.

Plants may be treated with the diluted, ready-to-use pesticidal formulation by contacting the plant to be treated with the diluted composition in any manner conventionally used. As used herein, the term "plant" refers not only to the stem, leave and fruit of the plant, visible above ground, but also to the roots as well as seeds. The amount of active ingredient contacted with the plant is preferably sufficient for the active ingredient to exercise its pesticidal or plant growth regulating activity, i.e. an effective amount.

II. Fungicide Formulations

The present disclosure provides formulations of fungicides. The fungicide formulation may be in solid or liquid form. Fungi against which the formulation may be employed include: Basidiomycetes, Ascomycetes, Adalomycetes or Fungi imperfecti-type fungi, especially heifers, oidia, eyespot, fusarioses, *Fusarium roseum, Fusarium nivale*, net blotch, leaf blotch, *Septoria* spot and sin *Rhizoctonia*. These harmful fungi can cause diseases in most vegetables and plants, but especially in cereals such as wheat, barley, rye, oats or their hybrids, and rice and corn.

The fungicide formulation may include a fungicide, an emulsifier component, such as one or more surfactants or co-surfactants chosen from one or more surfactant classes, an optional co-emulsifier, and an optional carrier agent, such as a solvent or solid carrier.

1. Fungicide

The fungicidal formulation includes a fungicide. Suitable fungicides include, but are not limited to: azoxystrobin, benalaxyl, carbendazim, chlorothalonil, cupfer, cymoxanil, cyproconazol, diphenoconazol, dinocap, epoxyconazol, fluazinam, flusilazol, flutriafol, folpel, fosetyl alumnium, kresoxim methyl, hexaconazol, mancozeb, metalaxyl, metconazol, myclobutanil, ofurace, phentinhydroxide, prochloraz, pyremethanil, soufre, tebucanazol and tetraconazol, and mixtures thereof. Suitable herbicides include, but are not limited to: alachlor, acloniphen, acetochlor, amidosulfuron, aminotriazol, atrazin, bentazon, biphenox, bromoxyl octanoate, bromoxynil, clethodim, chlodinafop-propargyl, chloridazon, chlorsulfuron, chlortoluron, clomazon, cycloxydim, desmedipham, dicamba, dicyclofop-methyl, diurea, diflupenicanil, dimithenamid, ethofumesat, fluazifop, fluazifop-p-butyl, fluorochloridon, fluroxypyr, glufosinat, glyphosate, galoxyfop-R, ioxynil octanoate, isoproturon, isoxaben, metamitron, metazachlor, metolachlor, metsulfuron-methyl, nicosulfuron, notflurazon, oryzalin, oxadiazon, oxyfluorphen, paraquat, pendimethalin, phenmedipham, phenoxyprop-p-ethyl, propaquizafop, prosulfocarb, quizalofop, sulcotrion, sulphosat, terbutylazin, triasulfuron, trichlorpyr, triflualin and triflusulforon-methyl which may be used individually or in admixture with one another.

The amount of fungicide may be about 1 wt. % or greater, about 5 wt. % or greater, about 10 wt. % or greater, about 20 wt. % or greater, about 30 wt. % or greater, about 40 wt. % or greater, or about 50 wt. % or less, about 60 wt. % or less, or about 70 wt. % or less, about 80 wt. % or less, about 90 wt. % or less, or any range combination using these endpoints, based on the total weight of the liquid fungicidal formulation.

2. Surfactant

The fungicide formulations of the present invention comprise one or more surfactants, also referred to as the surfactant system. The surfactant system may be used as a dispersing or wetting agent. The surfactant system may also be used as an emulsifier component to form a stable emulsion of the liquid fungicide formation when prepared for agricultural applications. The emulsifier component may also be used to form a stable emulsifiable concentrate. The surfactant system comprises at least one surfactant, which may be an amphoteric surfactant, a zwitterionic surfactant, a cationic surfactant, a nonionic surfactant, and optionally at least one other surfactant, which may be an amphoteric surfactant, a zwitterionic surfactant, a cationic surfactant, a nonionic surfactant, or a combination thereof.

Suitable surfactants for use in the fungicidal formulations of the present disclosure include one or more surfactants and/or co-surfactants of Formula I,

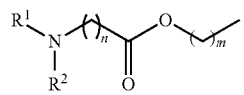

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide.

In particular, suitable surfactants or co-surfactants may include one or more of any of Surfactants 1-5 described herein.

The total amount of the one or more surfactants in the fungicidal formulation may be about 1 wt. % or greater, about 5 wt. % or greater, about 10 wt. % or greater, or about 15 wt. % or less, about 20 wt. % or less, about 25 wt. % or less, about 30 wt. % or less, about 35 wt. % or less, or within any range using these endpoints.

3. Co-Emulsifier or Co-Surfactant

The fungicide composition may include an optional co-emulsifier or co-surfactant. The optional co-surfactant may be an anionic surfactant and/or a non-ionic surfactant, and may include those surfactants of the present disclosure, as well as others. For example, the anionic surfactant include the surfactants of the present disclosure or any known in the art, and may include alkali, alkaline earth or ammonium salts of fatty acids, such as potassium stearate, alkyl sulfates, alkyl ether sulfates, alkylsulfonates or iso-alkylsulfonates, alkylnaphthalenesulfonates, alkyl methyl ester sulfonates, acyl glutamates, alkylsulfosuccinates, sarcosinates such as sodium lauroyl sarcosinate or taurates, and combinations thereof. The anionic surfactant may be present in the emulsifier component in any amount.

The non-ionic emulsifier may include those surfactants of the present disclosure or any known in the art, such as alkoxylated animal or vegetable fats and oils such as corn oil ethoxylates, soybean oil ethoxylates, castor oil ethoxylates, tallow fatty ethoxylates, glycerol esters such as glycerol monostearate, fatty alcohol alkoxylates and oxoalcohol alkoxylates, fatty acid alkoxylates such as oleic acid ethoxylates, alkylphenol alkoxylates such as isononylphenol ethoxylates, fatty amine alkoxylates, fatty acid amide alkoxylates, sugar surfactants such as sorbitan fatty acid esters (e.g. sorbitan monooleate, and sorbitan tristearate), polyoxyethylene sorbitan fatty acid esters, alkyl polyglycosides, N-alkylgluconamides, alkylmethyl sulfoxides, alkyldimethylphosphine oxides such as tetradecyldimethylphosphine oxide, and combinations thereof.

4. Carrier Agent

The fungicidal formulation of the present disclosure may include a carrier agent. As used herein, the term "carrier" refers to a material of natural or synthetic, organic or inorganic form which, when combined with the active ingredient, promotes its application to the plant, seeds or soil. Therefore, this carrier is usually inert, but must also be agriculturally acceptable, especially for the plant to be treated. The carrier may be solid (clay, natural or synthetic silicates, silicon dioxide, resins, waxes or solid fertilizers, etc.) or liquid (water, alcohols, ketones, petroleum fractions, aromatic or paraffinic hydrocarbons, chlorinated hydrocarbons, liquefied gases, etc.).

5. Other Additives

The fungicide formulation may include other additives such as stabilizers, penetrants, spreading agents, wetting agents, building agents, extending agents, emulsifiers, dispersants, suspending agents, plant penetrants, translocators, oils, activators, foliar nutrients, compatibility agents, drift retardants, foam retardants, buffers, inverting agents, soil penetrants, stabilizing agents, UV filters, feeding stimulants, washing agents, sinking agents, binders, liquid carriers, dry carriers such as attapulgite, kaolinite, vermiculite, starch polymers, corn cob, and combinations thereof. The pesticide formulation may also include additional chemical compounds that are not pesticides, such as activators, antifeedants, anti-fouling agents, attractant agents, chemosterilants, disinfectant agents, fumigant agents, pheromones, repellent agents, defoliants, desiccants, insect growth regulators, plant growth regulators, synergists, adjuvants, and combinations thereof.

These additives may be independently present in the pesticidal formulation in an amount of about 0 wt. % greater, about 5 wt. % or greater, about 10 wt. % or greater, about 15 wt. % or greater, or about 20 wt. % or lower, about 25 wt. % or lower, about 30 wt. % or lower, or within any range using these endpoints.

6. Fungicidal Emulsion

The liquid fungicidal formulation may be added to water or another solvent to form an agricultural emulsion at point of sale and/or use. Typically, well-formed agricultural emulsions are milky in color, spontaneously bloom (i.e., form), and have sufficient stability for efficacious application. However, the fungicidal emulsions of the present disclosure are not limited to such parameters and may have other characteristics that are indicative of successful emulsion formation.

The present disclosure provides an aqueous fungicidal formulation that includes the aforementioned fungicidal formulation and water. The liquid fungicide formulation may be combined with the water in a spray tank or in an independent tank prior to addition to a spray tank. For example, the liquid fungicide formulation may be added to an independent container and/or a spray tank with the water or separate from the water. The terminology "diluted" describes that the agricultural liquid fungicidal formulation including the water.

The water of the diluted fungicidal formulation may be present in an amount of about 5 wt. % or greater, about 10 wt. % or greater, about 20 wt. % or greater, about 30 wt. % or greater, about 40 wt. % or greater, about 50 wt. % or greater, or about 60 wt. % or lower, about 70 wt. % or lower, about 80 wt. % or lower, about 90 wt. % or lower, about 99 wt. % or lower, about 99.5 wt. % or lower, or within any range using these endpoints, of the diluted fungicidal formulation.

The fungicide may be present in the diluted fungicidal formulation in amounts from about 0.00001 wt. % or greater, about 0.0001 wt. % or greater, about 0.001 wt. % or greater, about 0.01 wt. % or greater, about 0.1 wt. % or greater, about 1 wt. % or greater, or about 2 wt. % or lower, about 4 wt. % or lower, about 6 wt. % or lower, about 8 wt. % or lower, about 10 wt. % or lower, or within any range using these endpoints.

The fungicide may be present in an amount (or in an amount equivalent to) of about 100 g/hectare or greater, about 200 g/hectare or greater, about 300 g/hectare or greater, about 400 g/hectare or greater, about 500 g/hectare or greater, or about 600 g/hectare or lower, about 700 g/hectare or lower, about 800 g/hectare or lower, about 900 g/hectare or lower, about 1000 g/hectare or lower, or within any range using these endpoints.

7. Emulsifiable Concentrate

The present disclosure provides a fungicidal emulsion that may be formed using an emulsifiable concentrate (also known in the art as an "EC"). The liquid fungicidal composition described above may be further described as an EC or may not be an EC. The emulsifiable concentrate may be a liquid that has a viscosity of about 1 cps or greater, 20 cps or greater, 40 cps or greater, 60 cps or greater, 80 cps or greater, 100 cps or greater, or 120 cps or lower, 140 cps or lower, 160 cps or lower, 180 cps or lower, 200 cps or lower, or within any range using these endpoints, at 25° C. to 200, 50 to 200, 100 to 200, or less than or equal to about 200, cps at 25° C. Without intending to be bound by any particular theory, it is believed that a viscosity of less than or equal to about 200 cps at 25° C. promotes blooming and efficient formation of an emulsion when the emulsifiable concentrate is used.

The emulsifiable concentrate itself may be anhydrous, i.e., free of water. Alternatively, the emulsifiable concentrate may include water. The emulsifiable concentrate may include water in an amount of 5 wt. % or less, 2.5 wt. % or less, 1 wt. % or less, 0.5 wt. % or less, or 0.1 wt. % or less. The emulsifiable concentrate may include less than 15, 14, 13, 12, 11, 10, 9, 8, 7, 6, 5, 4, 3, 2, or 1, part by weight of water per 100 parts by weight of the emulsifiable concentrate. The emulsifiable concentrate is a single oil-like, e.g. hydrophobic, phase that does not include water. When added to water or another solvent, the emulsifiable concentrate may form a milky white agricultural emulsion that blooms and that has little to no phase separation, as is described in greater detail below.

The emulsifiable concentrate may include a single phase. In other words, the emulsifiable concentrate may not include a distinct non-polar phase and a distinct polar phase but instead a single phase that includes the active component (the fungicide), the surfactant system, the optional co-surfactant, and/or the optional water-insoluble solvent. It is to be appreciated that the single phase may include partial phase separation but does not typically include total phase separation. At low temperatures, phase separation may occur. The emulsifiable concentrate may be described as including or being the aforementioned surfactant system and the fungicide (e.g. without the optional solvent and/or without the optional co-surfactant.

8. Solid Formulation

For solid form compositions, reference may be made to powders or dispersions suitable for dusting, in particular particulate compositions which are extruded, extruded, or extruded. The solid formulations may be formed through impregnation of a carrier powder with the active agent, or by granulation of a powder.

The amount of active agent in these granular compositions may be about 1 wt. % or greater, 10 wt. % or greater, 20 wt. % or greater, 30 wt. % or greater, of about 40 wt. % or lower, about 50 wt. % or lower, about 60 wt. % or lower, about 70 wt. % or lower, about 80 wt. % or lower, or within any range using these endpoints.

Wettable powder formulations (or spray powders) may include the active agent in an amount of about 20 wt. % or greater, about 30 wt. % or greater, about 40 wt. % or greater, or about 50 wt. % or greater, about 60 wt. % or lower, about 70 wt. % or lower, about 80 wt. % or lower, about 90 wt. % or lower, about 95 wt. % or lower, or within any range using these endpoints.

Wettable powder formulations may include wetting agents, such as a surfactant, which may include those surfactants of the present disclosure, in an amount of about 0 wt. % or greater, about 1 wt. % or greater, about 2 wt. % or greater, or about 3 wt. % or lower, about 4 wt. % or lower, about 5 wt. % or lower, or within any range using these endpoints.

Wettable powder formulations may include a dispersant, such as a surfactant, which may include those surfactants of the present disclosure, in an amount of about 3 wt. % or greater, about 4 wt. % or greater, about 5 wt. % or greater, about 6 wt. % or greater, or about 7 wt. % or lower, about 8 wt. % or lower, about 9 wt. % or lower, or about 10 wt. % or lower, or within any range using these endpoints.

Wettable powder formulations may include a solid carrier, which may include any solid carrier known in the art, in an amount or about 0 wt. % or greater, about 1 wt. % or greater, about 2 wt. % or greater, about 3 wt. % or greater, about 4 wt. % or greater, about 5 wt. % or greater, or about 6 wt. % or lower, about 7 wt. % or lower, about 8 wt. % or lower, about 9 wt. % or lower, about 10 wt. % or lower, or within any range using these endpoints.

Wettable powder formulations may contain one or more stabilizers and/or other additives, such as pigments, colorants, permeation agents, adhesion promoters or anti-caking agents.

In order to produce these wettable powder formulations or sprayable powders, the active agent(s) are intimately mixed with the other components in a suitable mixing apparatus, and the resulting mixture is milled with mills or other suitable grinding equipment. Thus, sprayable powders are obtained which have a wettability and suspendability. Thus, they can be suspended in arbitrary concentrations in water, and these suspensions are particularly useful for treating seeds in particular.

In addition to wettable powder formulations, pastes may also be produced. The conditions and methods of preparation and use of the pastes are similar to those for wettable powders or spray powders.

Dispersible granular compositions may be prepared by agglomeration in a suitable granulation system to provide powder compositions similar to wettable powder formulations.

III. Herbicide Formulation

The present disclosure further provides formulations of herbicides. These formulations may be applied to a plant in a herbicidally effective amount, and can effectively control one or more plant species of one or more of the following genera without restriction: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea*.

The herbicidal formulations of the present disclosure may include an herbicide, and optional second herbicide, one or more surfactants chosen from one or more surfactant classes, a water-insoluble solvent, and water.

1. Herbicide

The herbicide formulation of the present disclosure may include herbicides or their water-soluble salts. Suitable herbicides may include 2,4-D (2,4-dichlorophenoxyacetic acid), 2,4-DB (4-(2,4-dichlorophenoxy)butyric acid), am inocyclopyrachlor, am inopyralid, clopyralid, dicamba, glyphosate, MCPA, MCPB, picloram, triclopyr, or mixtures thereof.

The water-soluble salts of the herbicides herbicides may include salts containing one or more cations selected from the class of organo ammonium cations, wherein the organo ammonium cations may have from 1 to about 12 carbon atoms, such as organo ammonium cations include, for example, isopropyl ammonium, diglycol ammonium (2-(2-aminoethoxy)ethanol ammonium), dimethyl ammonium, diethyl ammonium, triethyl ammonium, monoethanol ammonium, dimethylethanol ammonium, diethanol ammonium, triethanol ammonium, triisopropanol ammonium, tetramethyl ammonium, tetraethylammonium, N,N,N-trimethylethanol ammonium (choline), and N,N-bis-(3-aminopropyl)methyl ammonium (BAPMA).

Additionally, the water-soluble salts of the herbicides may include salts containing one or more cations selected from inorganic cations such as, for example, sodium and/or potassium.

In the case of acidic herbicides, such as auxin herbicides, the herbicide may be present in the herbicide formulation in an amount of about 100 grams acid equivalent per liter (g ae/L) or greater, about 200 g ae/L or greater, about 300 g ae/L or greater, or about 400 g ae/L or lower, about 500 g ae/L or lower, about 600 g ae/L or lower, about 625 g ae/L or lower, or within any range using these endpoints.

Some herbicide active agents described herein do not contain an acid-type functional group and, for these active ingredients, the terms "acid equivalent" and "acid equivalent basis" are not accurate to describe the amount of the second herbicide present. Generally, in such instances, the terms "active ingredient" or "active ingredient basis" can be used to describe the amount of the second herbicide active ingredient present. For example, grams active ingredient per liter (g ai/L) may be used in place of grams acid equivalent per liter (g ae/L), or grams active ingredient per kilogram (g ai/kg) may be used in place of grams acid equivalent per kilogram (g ae/kg) when the active ingredient does not have an acid equivalent.

2. Optional Second Herbicide

Suitable second herbicides may be selected from, but are not limited to, esters of 4-CPA, 4-CPB, 4-CPP, 2,4-D, 3,4-DA, 2,4-DB, 3,4-DB, 2,4-DEB, 2,4-DEP, 3,4-DP, 2,4,5-T, 2,4,5-TB, and 2,3,6-TBA, allidochlor, acetochlor, acifluorfen, aclonifen, alachlor, alloxydim, alorac, ametridione, ametryn, am ibuzin, am icarbazone, am idosulfuron, am inocyclopyrachlor esters, am inopyralid esters, am iprofosmethyl, am itrole, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicylopyrone, bifenox, bilanafos, bispyribac, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cafenstrole, cafenstrole, cambendichlor, carbasulam, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, clomeprop, cloprop, cloproxydim, clopyralid esters, cloransulam, CPMF, CPPC, credazine, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba esters, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinitramine, dinofenate, dinoprop, dinosam, dinoseb, dinoterb, diphenamid, dipropetryn, diquat, disul, dithiopyr, diuron, DMPA, DNOC, EBEP, eglinazine, endothal, epronaz, epronaz, EPTC, erbon, esprocarb, ethalfluralin, ethametsulfuron, ethidimuron, ethiolate, ethofumesate, ethoxyfen, ethoxysulfuron, etinofen, etnipromid, etnipromid, etnipromid, etobenzanid, EXD, fenasulam, fenasulam, fenasulam, fenoprop, fenoxaprop, fenoxaprop-P, fenoxasulfone, fenteracol, fenthiaprop, fentrazamide, fenuron, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupoxam, flupropacil, flupropanate, flupyrsulfuron, fluridone, fluorochloridone, non-liquid fluoroxypyr esters, fluoroxypyr-meptyl, flurtamone, fluthiacet, fomesafen, fomesafen, foramsulfuron, fosamine, furyloxyfen, glyphosate, halauxfen, halauxfen-methyl, halosafen, halosafen, halosulfuron, haloxydine, haloxyfop, haloxyfop-P, hexazinone, imazamethabenz, imazamox, imazapic, imazapyr, imazaquin, imazethapyr, imazosulfuron, indanofan, indaziflam, iodobonil, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MCPA esters, MCPA-thioethyl, MCPA-EHE, MCPB esters, mecoprop, mecoprop-P, medinoterb, mefenacet, mefluidide, mesoprazine, mesosulfuron, mesotrione, metam, metamifop, metamifop, metamitron, metazachlor, metazosulfuron, metflurazon, methabenzthiazuron, methalpropalin, methazole, methiobencarb, methiozolin, methiuron, methiuron, methometon, methoprotryne, methyldymron, metobenzuron, metobromuron, metolachlor, S-metolachlor, metosulam, metoxuron, metribuzin, metsulfuron, molinate, monalide, monisouron, monolinuron, monuron, morfamquat, naproanilide, napropamide, naptalam, neburon, nicosulfuron, nipyraclofen, nitralin, nitrofen, nitrofluorfen, norflurazon, noruron, OCH, orbencarb, orthosulfamuron, oryzalin, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentanochlor, pentoxazone, perfluidone, pethoxamid, phenisopham, phenmedipham, phenmedipham-ethyl, phenobenzuron, picloram esters, picolinafen, pinoxaden, piperophos, pretilachlor, primisulfuron, procyazine, prodiamine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyrosulfotole, pyroxasulfone, pyroxsulam, quinclorac, quinmerac, quinoclamine, quinonamid, quizalofop, quizalofop-P, rhodethanil, rimsulfuron, saflufenacil, sebuthylazine, secbumeton, sethoxydim, siduron, simazine, simeton, simetryn, sulcotrione, sulfallate, sulfentrazone, sulfometuron, sulfosulfuron, sulglycapin, swep, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, non-liquid triclopyr esters, thidiazimin, thidiazuron, thidiazuron, thiencarbazone-methyl, thifensulfuron, thiobencarb, tiocarbazil, tioclorim, topramezone, tralkoxydim, tri-allate, triasulfuron, triaziflam, tribenuron, tricamba, tridiphane, trietazine, trifloxysulfuron, trifluralin, triflusulfuron, trifop, trifopsime, trihydroxytriazine, trimeturon, tripropindan, tritac, tritosulfuron, vernolate, xylachlor and mixtures and derivatives thereof.

The second herbicide is present, if used, in an amount of about 0 g ae/L or greater, 0.1 g ae/L or greater, 10 g ae/L or greater, 50 g ae/L or greater, 100 g ae/L or greater, or 200 g ae/L or lower, about 300 g ae/L or lower, about 400 g ae/L or lower, or within any range using these endpoints.

Some second herbicide active agents described herein do not contain an acid-type functional group and, for these active ingredients, the terms "acid equivalent" and "acid equivalent basis" are not accurate to describe the amount of the second herbicide present. Generally, in such instances, the terms "active ingredient" or "active ingredient basis" can be used to describe the amount of the second herbicide active ingredient present. For example, grams active ingredient per liter (g ai/L) may be used in place of grams acid equivalent per liter (g ae/L), or grams active ingredient per kilogram (g ai/kg) may be used in place of grams acid equivalent per kilogram (g ae/kg) when the active ingredient does not have an acid equivalent.

3. Surfactant

Suitable surfactants for use in the herbicide formulations of the present disclosure include one or more surfactants and/or co-surfactants of Formula I,

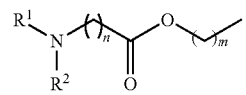

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide.

In particular, suitable surfactants or co-surfactants may include one or more of any of Surfactants 1-5 described herein.

The herbicidal formulations may include one or more surfactants in an amount of about 0 wt. % or greater, about 2 wt. % or greater, about 4 wt. % or greater, about 6 wt. % or greater, about 8 wt. % or greater, or about 10 wt. % or lower, about 12 wt. % or lower, about 14 wt. % or lower, about 16 wt. % or lower, or within any range using these endpoints.

4. Water-Insoluble Solvents

Suitable water-insoluble immiscible organic solvents include those derived from or made from natural, non-petroleum sources such as, for example, plants and animals, and include, vegetable oils, seed oils, animal oils and the like, such N,N-dimethylcaprylamide (N,N-dimethyloctanamide), N,N-dimethylcapramide (N,N-dimethyldecanamide), and mixtures thereof, which are available commercially as Agnique® AMD 810 and Agnique® AMD 10, from BASF Corp. (Florham Park, N.J.), Genegen® 4166, Genegen® 4231 and Genegen® 4296, from Clariant (Charlotte, N.C.), Hallcomid M-8-10 and Hallcomid M-10, from Stepan (Northfield, Ill.), and Amid DM10 and DM810 from AkzoNobel (Chicago, Ill.). Additional examples of naturally derived organic solvents include the morpholine amides of caprylic/capric fatty acids ($C_8$/$C_{10}$) which are commercially available as JEFFSOL® AG-1730 Solvent from Huntsman International LLC (The Woodlands, Tex.).

Other suitable water-insoluble solvents may include aromatic hydrocarbons, mixed naphthalene and alkyl naphthalene fractions, aromatic solvents, particularly alkyl substituted benzenes such as xylene or propylbenzene fractions, and the like; $C_1$-$C_6$ esters of fatty acids derived from vegetable, seed or animal oils such as, methyl caproate, methyl caprylate, methyl caprate, methyl laurate, methyl myristate, methyl palmitate, methyl stearate, methyl oleate, methyl linoleate, methyl linolenate, and the like; ketones such as isophorone and trimethylcyclohexanone (dihydroisophorone); acetate esters such as, methyl, ethyl, propyl, butyl, pentyl, hexyl, or heptyl acetate, and the like; and cyclic alkyl carbonates such as propylene carbonate and butylene carbonate, which are available as the JEFFSOL® alkylene carbonates from Huntsman (The Woodlands, Tex.), and dibutyl carbonate, also from Huntsman, and mixtures of any of the water immiscible organic solvents described herein.

The water-insoluble solvent may be present in the herbicidal formulation in an amount of about 0 wt. % or greater, about 10 wt. % or greater, about 20 wt. % or greater, or about 30 wt. % or lower, about 40 wt. % or lower, about 50 wt. % or lower, or within any range using these endpoints.

5. Water

Water may be present in the herbicidal formulations of the present disclosure to serve as both an aqueous solvent and a carrier for the ingredients in the described compositions.

The herbicidal formulation of the present disclosure may include water in an amount of about 200 g/L or greater, about 300 g/L or greater, about 400 g/L or greater, or about 500 g/L or lower, about 600 g/L or lower, about 700 g/L or lower, about 800 g/L or lower, or within any range using these endpoints.

6. Other Additives

The herbicidal formulation may include one or more additional compatible ingredients. These additional ingredients may include, for example, one or more pesticides or other ingredients, which may be dissolved or dispersed in the composition and may be selected from acaricides, algicides, antifeedants, avicides, bactericides, bird repellents, chemosterilants, defoliants, desiccants, disinfectants, fungicides, herbicide safeners, herbicides, insect attractants, insecticides, insect repellents, mammal repellents, mating disrupters, molluscicides, nematicides, plant activators, plant growth regulators, rodenticides, semiochemicals, synergists, and virucides. Also, any other additional ingredients providing functional utility such as, for example, antifoam agents, antimicrobial agents, buffers, corrosion inhibitors, dispersing agents, dyes, fragrants, freezing point depressants, neutralizing agents, odorants, penetration aids, sequestering agents, spray drift control agents, spreading agents, stabilizers, sticking agents, viscosity-modifying additives, water soluble solvents and the like, may be included in these compositions.

When the described herbicidal formulations are used in combination with the additional active ingredients such as, for example, herbicide active ingredients, the compositions described herein can be formulated with the other active ingredient or active ingredients as premix concentrates, tank-mixed in water with the other active ingredient or active ingredients for spray application or applied sequentially with the other active ingredient or active ingredients in separate spray applications.

7. Method of Making

The herbicide formulations of the present disclosure may be prepared by the steps of: 1) preparing a solution of the one or more second herbicide in the organic solvent and a surfactant; 2) adding the solution prepared in step 1) to a concentrated solution of a water-soluble salt of an herbicide in water with good mixing to form a clear solution; and 3) optionally, adding any additional compatible active or inert ingredients.

Alternatively, the herbicide formulations of the present disclosure may be prepared by the steps of: 1) providing a second herbicide that is a liquid and, optionally, mixing it with the organic solvent and a surfactant; 2) adding the composition prepared in step 1) to a concentrated solution of a water-soluble salt of an herbicide in water with good mixing to form a clear solution; and 3) optionally, adding any additional compatible active or inert ingredients.

Suitable water compatible ingredients that may be added to the herbicide formulations include, but are not limited to, water soluble or water insoluble dispersing surfactants, such as the surfactants of the present disclosure, water insoluble active ingredients and optionally, other inert ingredients such as pH buffers, wetting agents, antifreeze agents, antifoam agents, and biocides.

8. Method of Use

The aqueous herbicidal formulations described herein may optionally be diluted in an aqueous spray mixture for agricultural application such as for weed control in crop fields or in turf. Such herbicidal formulations are typically diluted with an inert carrier, such as water, before application. The diluted herbicidal formulations, which are usually applied, for example, to weeds, the locus of weeds, or the locus of where weeds may eventually emerge, may contain the agriculturally active agent (the herbicide) in an amount of about 0.0001 wt. % or greater, about 0.001 wt. % or greater, about 0.01 wt. % or greater, about 0.1 wt. % or greater, about 1 wt. % or greater, or about 2 wt. % or lower, about 3 wt. % or lower, about 4 wt. % or lower, or about 5 wt. % or lower, or within any range using these endpoints. The herbicide formulations of the present disclosure can be applied, for example, to weeds or their locus by the use of conventional ground or aerial sprayers, by addition to irrigation water and by other conventional means known to those skilled in the art.

The herbicide formulations of the present disclosure may be used in controlling undesirable vegetation in crops possessing single, multiple or stacked genomic traits conferring tolerance to one or more herbicide chemistries and/or inhibitors with single or multiple modes of action.

IV. Insecticide Formulations

The present disclosure also provides formulations of insecticides. Such formulations may be in liquid or solid forms, such as emulsifiable concentrates, oil in water (O/W) emulsions, suspension concentrates, and wettable powders.

The insecticide formulation may include an insecticide, one or more surfactants chosen from one or more surfactant classes, an optional antifoaming agent, an optional antifreezing agent, and water.

1. Insecticide

Suitable insecticides may include one or more of pyrethroids, such as a synthetic pyrethroid; an organophosphate compound, such as chlorpyrifos-ethyl, chlorpyrifos-methyl, pirimiphos-methyl, fenitrothion; a phenyl ether such as pyriproxyfen; a benzoylurea, such as flufenoxuron; a carbamate, such as fenoxycarb, carbosulfan; nicotinoids, such as acetamiprid; pyridinecarboxamides, such as flonicamid; and/or others. The pyrethroid may be selected from one or more of bifenthrin, zeta-cypermethrin, alpha-cypermethrin, tetra-methrin, lambda-cyhalothrin, fenvalerate, cyfluthrin, bio-resmethrin, permethrin, delta-methrin.

The insecticide may be present in the insecticide formulation in an amount, measured in weight per volume, of about 1% or greater, about 5% or greater, about 10% or greater, or about 15% or less, about 20% or less, or within any range using these endpoints.

2. Surfactants

The insecticide formulation may include one or more surfactants chosen from one or more surfactant classes, collectively referred to as the surfactant system.

Suitable surfactants for use in the insecticide formulations of the present disclosure include one or more surfactants and/or co-surfactants of Formula I,

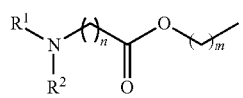

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide.

In particular, suitable surfactants or co-surfactants may include one or more of any of Surfactants 1-5 described herein.

The surfactant system may be present in the insecticide formulation in an amount, measured in weight per volume, of about 1% or greater, about 5% or greater, about 10% or greater, about 15% or greater, or about 20% or less, about 25% or less, about 30% or less, about 35% or less, about 40% or less, or within any range using these endpoints.

3. Optional Antifoaming Agent

The optional antifoaming agent in the insecticide formulation may include silicone emulsions, and/or surfactants, such as the surfactants of the present disclosure.

The antifoaming agent may be present in the insecticide formulation in an amount, measured in weight per volume, of about 0.0% or greater, about 0.1% or greater, about 0.2% or greater, about 0.3% or greater, about 0.4% or greater, about 0.5% or greater, or about 0.6% or lower, about 0.7% or lower, about 0.8% or lower, about 0.9% or lower, about 1.0% or lower, or within any range using these endpoints.

4. Optional Antifreezing Agent

The insecticide formulation may include an optional antifreezing agent. Suitable antifreezing agents may include diols, such as alkyldiols or dialkyldiols.

The insecticide formulation may include an antifreezing agent in an amount, measured in weight per volume, of about 0% or greater, about 1% or greater, about 2% or greater, about 3% or greater, about 4% or greater, about 5% or greater, or about 6% or lower, about 7% or lower, about 8% or lower, about 9% or lower, about 10% or lower, or within any range using these endpoints.

5. Water

The insecticide formulation may include water in an amount, measured in weight per volume, of about 25% or greater, about 30% or greater, about 35% or greater, about 40% or greater, about 45% or greater, about 50% or greater, about 55% or greater, or about 60% or lower, about 65% or lower, about 70% or lower, about 75% or lower, about 80% or lower, about 85% or lower, about 90% or lower, about 95% or lower, about 98% or lower, or within any range using these endpoints.

6. Other Additives

The insecticide formulations of the present disclosure may include viscosity modifiers. Such viscosity modifiers may include thickening agents, such as cellulose derivatives, polyacrylamides, polyvinyl alcohols, polyvinyl pyrollidones, and natural gums.

Viscosity modifiers may be present in the insecticidal formulation in any amount suitable to modify the viscosity to the desired level.

The insecticide formulations of the present disclosure may also include preservatives. Suitable preservatives include methylparaben.

Preservatives may be present in the insecticide formulation in an amount, measured as weight per volume, of 0.0% or greater, 0.1% or greater, or 0.2% or less, or within any range using these endpoints.

V. Adjuvants

In addition to the uses described above, the surfactants of the present disclosure may be used as adjuvants in formulations agriculturally active agents, such as pesticides, plant growth regulators, herbicides, fungicides, and insecticides. Adjuvant compounds may be employed to improve one or more properties of formulations of agriculturally active agents, such as for example, storage stability, ease of handling, pesticide efficacy against a target organism.

VI. Spray Drift Reducing Agents

Spray drift refers to the unintentional diffusion of pesticides and other agriculturally active agents, including off-target contamination. This can lead to damage in human health, environmental contamination, and property damage. The surfactants of the present disclosure may be used to reduce the amount of driftable fines of formulations of agriculturally active agents in both aerial and ground spray applications.

The surfactants of the present disclosure, and mixtures thereof, can be incorporated into an aqueous spray mixture, for example, by being tank-mixed directly with a diluted formulation of an agriculturally active agent, such as a pesticide, plant growth regulator, fungicide, herbicide, or insecticide.

The optimum spray droplet size depends on the application for which the composition is used. If droplets are too large, there will be less coverage by the spray, e.g., large droplets will land in certain areas while areas in between will receive little or no spray coverage. The maximum acceptable droplet size may depend on the amount of composition being applied per unit area and the need for uniformity in spray coverage. Smaller droplets provide more even coverage, but are more prone to drift during spraying. Thus, application parameters such as uniformity in spray coverage must be balanced against the tendency for smaller droplets to drift. For example, if it is particularly windy during spraying, larger droplets may be needed to reduce drift, whereas on a calmer day, smaller droplets may be acceptable. In addition to the physical properties of a particular aqueous composition, spray droplet size may also depend on the spray apparatus, e.g., nozzle size and configuration.

The reduction in spray drift may result from a variety of factors including a reduction in the production of fine spray droplets (<150 μm minimum diameter) and an increase in the volume median diameter (VMD) of the spray droplets. In any event, for a given spray apparatus, application, and conditions, and based on the surfactant used, the median diameter of the plurality of spray droplets created using the surfactants described herein is increased above that of a spray composition that does not include the surfactants of the present disclosure.

VII. Surfactants

The present disclosure provides surfactants for use in agricultural products in the form of derivatives of amino acids. The amino acids may be naturally occurring or synthetic, or they may be obtained from ring-opening reactions of lactams, such as caprolactam. The compounds of the present disclosure have been shown to have surface-active properties, and may be used as surfactants and wetting agents, for example. In particular, the present disclosure provides compounds of Formula I, Formula I 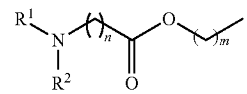 wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide.

One specific compound provided by the present disclosure is 6-(dodecyloxy)-N,N,N-trimethyl-6-oxohexan-1-aminium iodide (Surfactant 1), having the following formula:

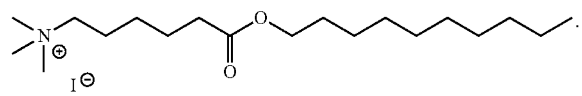 [SMILES: CCCCCCCCCCOC(=O)CCCCC[N+](C)(C)C ; [I-]]

A second specific compound provided by the present disclosure is dodecyl 6-(dimethylamino)hexanoate N-oxide (Surfactant 2), having the following formula:

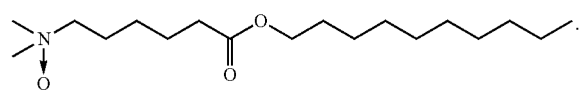 [SMILES: CCCCCCCCCCOC(=O)CCCCC[N+](C)(C)[O-]]

In the structure above, the notation "N→O" is intended to convey a non-ionic bonding interaction between nitrogen and oxygen.

A third specific compound provided by the present disclosure is 6-(dodecyloxy)-N,N-dimethyl-6-oxohexan-1-aminium chloride (Surfactant 3), having the following formula:

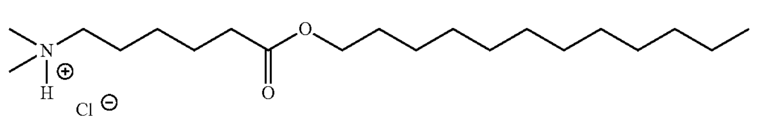

A fourth specific compound provided by the present disclosure is 4-((6-(dodecyloxy)-6-oxohexyl)dimethylammonio)butane-1-sulfonate (Surfactant 4), having the following formula:

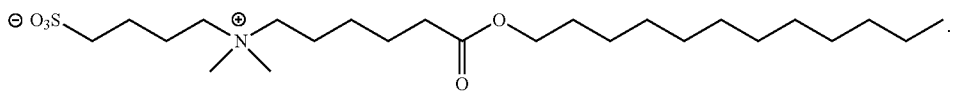

A fifth specific compound provided by the present disclosure is 6-(dodecyloxy)-6-oxohexan-1-aminium chloride (Surfactant 5), having the following formula:

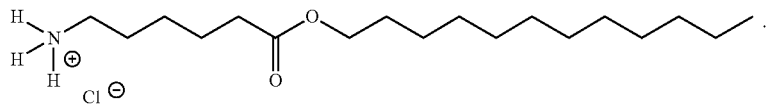 [SMILES: CCCCCCCCCCCCOC(=O)CCCCC[NH3+] ; [Cl-]]

These surfactants may be synthesized by various methods. One such method includes opening a lactam to yield an amino acid having an N-terminus and C-terminus. The N-terminus may be reacted with one or more alkylating agents and/or an acid to yield a quaternary ammonium salt. Alternatively, the N-terminus may be reacted with an oxidizing agent to yield an amine N-oxide. The C-terminus may be reacted with an alcohol in the presence of an acid to yield an ester.

The amino acid may be naturally occurring or synthetic or may be derived from a ring opening reaction of a lactam, such as caprolactam. The ring-opening reaction may be either an acid or alkali catalyzed reaction, and an example of an acid catalyzed reaction is shown below in Scheme 1.

SCHEME 1

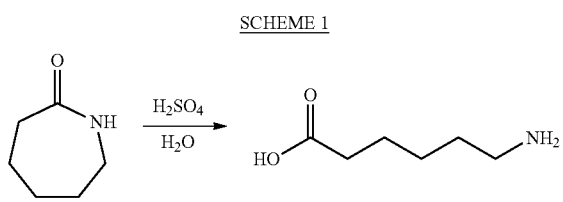 [SMILES: O=C1CCCCCN1 ; "H2SO4" ; O ; NCCCCCC(=O)O]

The amino acid may have as few as 1 or as many as 12 carbons between the N- and C-terminii. The alkyl chain may be branched or straight. The alkyl chain may be interrupted with nitrogen, oxygen, or sulfur. The alkyl chain may be further substituted with one or more substituents selected from the group consisting of hydroxyl, amino, amido, sulfonyl, sulfonate, carboxyl, and carboxylate. The N-terminal nitrogen may be acylated or alkylated with one or more alkyl groups. For example, the amino acid may be 6-(dimethylamino)hexanoic acid.

Surfactant 1 may be synthesized as shown below in Scheme 2. As shown, 6-aminohexanoic acid is treated with formaldehyde in formic acid at reflux to give 6-(dimethylamino)hexanoic acid. The free carboxylic acid is then treated with an alcohol, such as dodecanol, in the presence of p-toluene sulfonic acid (PTSA) in toluene to give the corresponding ester, dodecyl 6-(dimethylamino)hexanoate. The N-terminus is then alkylated with methyl iodide in the presence of sodium carbonate.

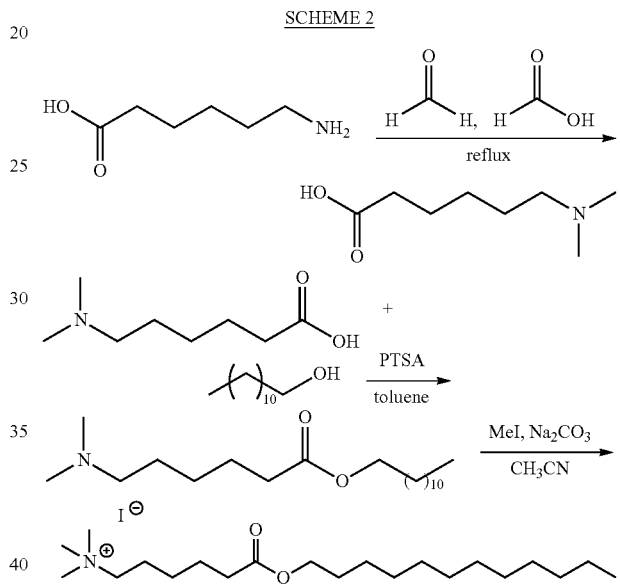

Surfactant 2 may be synthesized as shown below in Scheme 3. As shown, 6-aminohexanoic acid is treated with formaldehyde in formic acid at reflux to give 6-(dimethylamino)hexanoic acid. The free carboxylic acid is then treated with an alcohol, such as dodecanol, in the presence of p-toluene sulfonic acid (PTSA) in toluene to give the corresponding ester, dodecyl 6-(dimethylamino)hexanoate. The N-terminus is then oxidized with hydrogen peroxide to give the amine oxide.

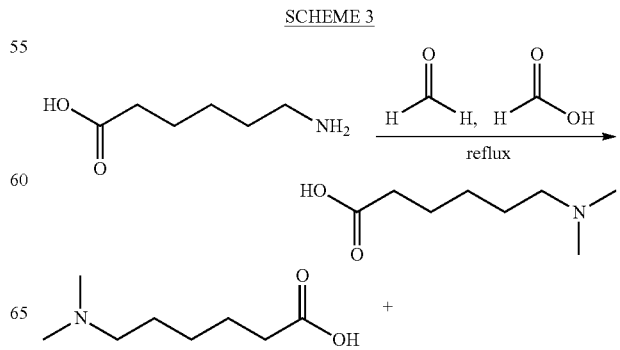

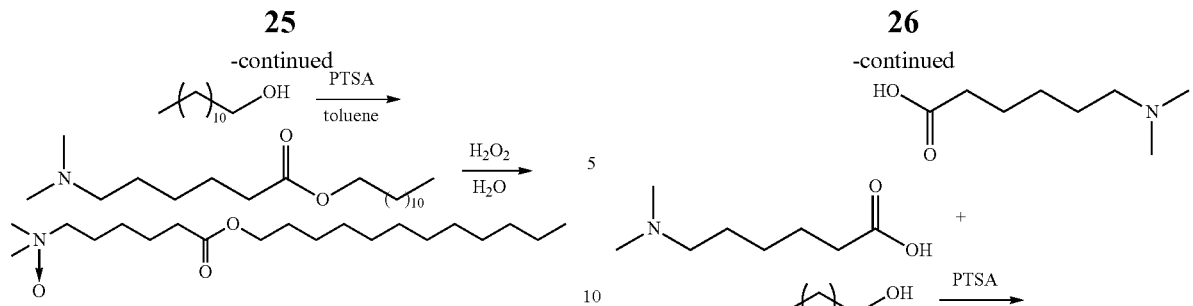

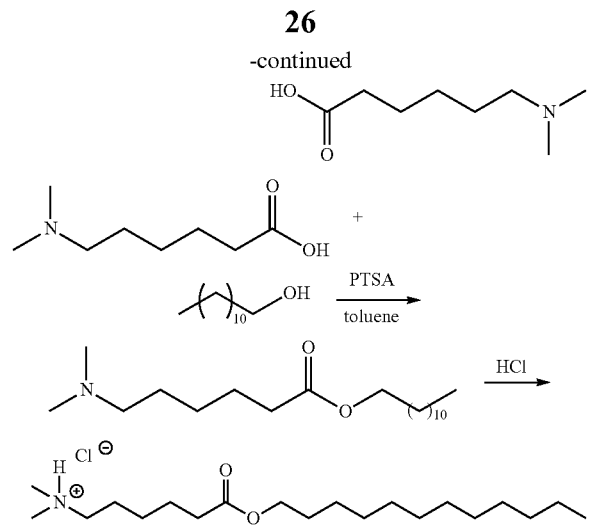

Surfactant 3 may be synthesized as shown below in Scheme 4. As shown, 6-aminohexanoic acid is treated with formaldehyde in formic acid at reflux to give 6-(dimethylamino)hexanoic acid. The free carboxylic acid is then treated with an alcohol, such as dodecanol, in the presence of p-toluene sulfonic acid (PTSA) in toluene to give the corresponding ester, dodecyl 6-(dimethylamino)hexanoate. The N-terminus is then alkylated with methyl iodide in the presence of sodium carbonate.

SCHEME 4

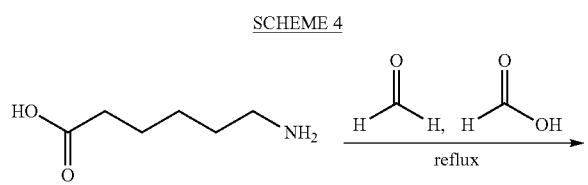

Surfactant 4 may be synthesized as shown below in Scheme 5. As shown, 6-aminohexanoic acid is treated with formaldehyde in formic acid at reflux to give 6-(dimethylamino)hexanoic acid. The free carboxylic acid is then treated with an alcohol, such as dodecanol, in the presence of p-toluene sulfonic acid (PTSA) in toluene to give the corresponding ester, dodecyl 6-(dimethylamino)hexanoate. The N-terminus is then treated with 1,4-butanesultone in refluxing ethyl acetate to yield the desired sulfonate.

SCHEME 5

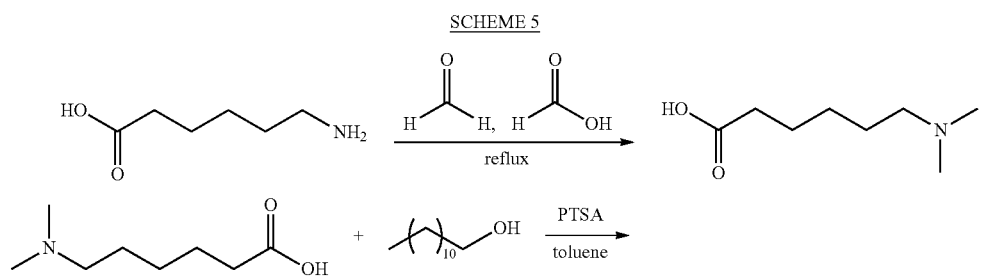

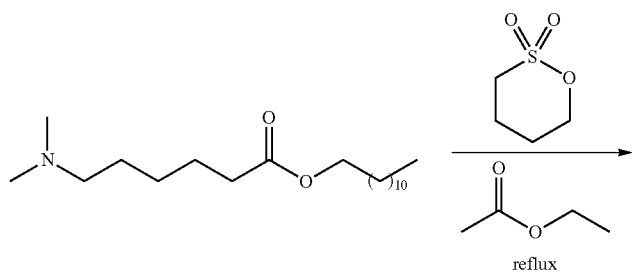

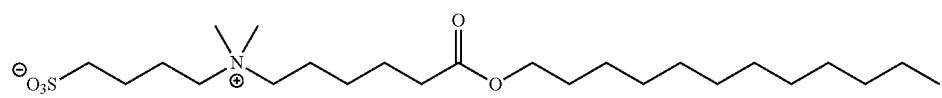

Surfactant 5 may be synthesized as shown below in Scheme 6. As shown, 6-aminohexanoic acid is reacted with an alcohol, in the presence of p-toluene sulfonic acid (PTSA) in toluene to give the corresponding ester, dodecyl 6-aminohexanoate. The N-terminus is protonated with hydrochloric acid to give the desired hydrochloride salt.

SCHEME 6

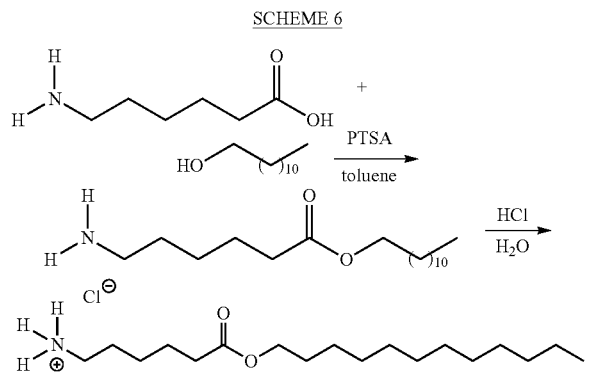

The compounds of the present disclosure demonstrate surface-active properties. These properties may be measured and described by various methods. One method by which surfactants may be described is by the molecule's critical micelle concentration (CMC). CMC may be defined as the concentration of a surfactant at which micelles form, and above which all additional surfactant is incorporated into micelles.

As surfactant concentration increases, surface tension decreases. Once the surface is completely overlaid with surfactant molecules, micelles begin to form. This point represents the CMC, as well as the minimum surface tension. Further addition of surfactant will not further affect the surface tension. CMC may therefore be measured by observing the change in surface tension as a function of surfactant concentration. One such method for measuring this value is the Wilhemy plate method. A Wilhelmy plate is usually a thin iridium-platinum plate attached to a balance by a wire and placed perpendicularly to the air-liquid interface. The balance is used to measure the force exerted on the plate by wetting. This value is then used to calculate the surface tension (γ) according to Equation 1:

$$\gamma = F/l \cos \theta \qquad \text{Equation 1:}$$

wherein l is equal to the wetted perimeter (2w+2d, in which w and d are the plate thickness and width, respectively) and cos θ, the contact angle between the liquid and the plate, is assumed to be 0 in the absence of an extant literature value.

Another parameter used to assess the performance of surfactants is dynamic surface tension. The dynamic surface tension is the value of the surface tension for a particular surface or interface age. In the case of liquids with added surfactants, this can differ from the equilibrium value. Immediately after a surface is produced, the surface tension is equal to that of the pure liquid. As described above, surfactants reduce surface tension; therefore, the surface tension drops until an equilibrium value is reached. The time required for equilibrium to be reached depends on the diffusion rate and the adsorption rate of the surfactant.

One method by which dynamic surface tension is measured relies upon a bubble pressure tensiometer. This device measures the maximum internal pressure of a gas bubble that is formed in a liquid by means of a capillary. The measured value corresponds to the surface tension at a certain surface age, the time from the start of the bubble formation to the occurrence of the pressure maximum. The dependence of surface tension on surface age can be measured by varying the speed at which bubbles are produced.

Surface-active compounds may also be assessed by their wetting ability on solid substrates as measured by the contact angle. When a liquid droplet comes in contact with a solid surface in a third medium, such as air, a three-phase line forms among the liquid, the gas and the solid. The angle between the surface tension unit vector, acting at the three-phase line and tangent at the liquid droplet, and the surface is described as the contact angle. The contact angle (also known as wetting angle) is a measure of the wettability of a solid by a liquid. In the case of complete wetting, the liquid is completely spread over the solid and the contact angle is 0°. Wetting properties are typically measured for a given compound at the concentration of 1-100×CMC, however, it is not a property that is concentration-dependent therefore measurements of wetting properties can be measured at concentrations that are higher or lower.

In one method, an optical contact angle goniometer may be used to measure the contact angle. This device uses a digital camera and software to extract the contact angle by analyze the contour shape of a sessile droplet of liquid on a surface.

Potential applications for the surface-active compounds of the present disclosure include formulations for use as shampoos, hair conditioners, detergents, spot-free rinsing solutions, floor and carpet cleaners, cleaning agents for graffiti removal, wetting agents for crop protection, adjuvants for crop protection, and wetting agents for aerosol spray coatings.

It will be understood by one skilled in the art that small differences between compounds may lead to substantially different surfactant properties, such that different compounds may be used with different substrates, in different applications.

The following non-limiting embodiments are provided to demonstrate the different properties of the different surfactants. In Table 1 below, short names for the surfactants are correlated with their corresponding chemical structures.

TABLE 1

| Surfactant | Formula & Name |
| --- | --- |
| Surfactant 1 | <br>6-(Dodecyloxy)-N, N, N-trimethyl-6-oxohexan-1-aminium iodide |

TABLE 1-continued

| Surfactant | Formula & Name |
|---|---|
| Surfactant 2 | Dodecyl 6-(dimethylamino)hexanoate N-oxide |
| Surfactant 3 | 6-(Dodecyloxy)-N, N-dimethyl-6-oxohexan-1-aminium chloride |
| Surfactant 4 | 4-((6-(Dodecyloxy)-6-oxohexyl)dimethylammonio)butane-1-sulfonate |
| Surfactant 5 | 6-(Dodecyloxy)-6-oxohexan-1-aminium chloride |

Each of the five compounds are effective as surface-active agents, useful for wetting or foaming agents, dispersants, emulsifiers, and detergents, among other applications.

Surfactant 1, Surfactant 3, and Surfactant 5 are cationic. These surfactants are useful in both the applications described above and some further special applications such as surface treatments, such as in personal hair care products, and can also be used to generate water repellant surfaces.

Surfactant 4 is non-ionic, and can be used in shampoos, detergents, hard surface cleaners, and a variety of other surface cleaning formulations.

Surfactant 5 is zwitterionic. These surfactants are useful as co-surfactants in all of the applications described above.

EXAMPLES

Nuclear magnetic resonance (NMR) spectroscopy was performed on a Bruker 500 MHz spectrometer. The critical micelle concentration (CMC) was determined by the Wilhelmy plate method at 23° C. with a tensiometer (DCAT 11, DataPhysics Instruments GmbH) equipped with a Pt-Ir plate. Dynamic surface tension was determined with a bubble pressure tensiometer (Krüss BP100, Krüss GmbH), at 23° C. Contact angle was determined with the optical contact angle goniometer (OCA 15 Pro, DataPhysics GmbH) equipped with a digital camera.

Example 1a

Synthesis of 6-(dodecyloxy)-N,N,N-trimethyl-6-oxohexan-1-aminium iodide (Surfactant 1)

6-(Dimethylamino)hexanoic acid (11.99 g, 75.36 mmol) was dissolved in toluene (50 mL) in a round bottom flask equipped with a Dean-Stark trap. Dodecanol (12.68 g, 75.36 mmol) and p-toluene sulfonic acid monohydrate (PTSA) (14.33 g, 75.36 mmol) were then added. The reaction was heated to reflux for 24 hours, until no further water was noted in the Dean-Stark trap. The solvent was removed under vacuum and the resultant solid was washed with hexanes. The solid was dissolved in dichloromethane (200 mL) and washed with saturated sodium carbonate to give dodecyl 6-(dimethylamino)hexanoate in 51% yield. 1H NMR (DMSO) δ 4.00 (t, J=6.5 Hz, 2H), 2.27 (t, J=7.3 Hz, 2H), 2.13-2.16 (m, 2H), 2.01 (s, 6H), 1.54-1.53 (m, 6H), 1.27-1.18 (m, 20H), 0.86 (t, 3H).

Dodecyl 6-(dimethylamino)hexanoate (1.0 g, 3.05 mmol) was dissolved in acetonitrile (10 mL). Sodium carbonate (0.388 g, 3.66 mmol) was then added, and the reaction was stirred at room temperature for 10 minutes. Methyl iodide (0.57 mL, 9.16 mmol) was added, and the reaction mixture was heated to 40° C. for 24 hours, then cooled to room temperature. The mixture was filtered and concentrated to give 6-(dodecyloxy)-N,N,N-trimethyl-6-oxohexan-1-aminium iodide as a yellow solid in 92% yield. $^1$H NMR (DMSO) δ 4.00 (t, J=6.7 Hz, 2H), 3.30-3.22 (m, 2H), 3.04 (s, 9H), 2.34 (t, J=7.4 Hz, 2H), 1.70-1.63 (m, 2H), 1.62-1.46 (m, 4H), 1.31-1.20 (m, 20H), 0.86 (t, J=6.9 Hz, 3H).

Example 1b

Determination of Critical Micelle Concentration (CMC) of Surfactant 1

The critical micelle concentration (CMC) was tested. From the change in surface tension with concentration in water, the CMC was determined to be about 1 mmol. The plateau value of minimum surface tension that can be reached by this surfactant is about 33 mN/m, namely 33 mN/m±3.3 mN/m. FIG. 1 is a plot of these results, showing surface tension versus concentration. From the plot, the surface tension is about 34 mN/m the CMC and is about 33.8 mN/m at a concentration of 1.0 mmol or greater.

Example 1c

Determination of Dynamic Surface Tension of Surfactant 1

Figure 2:
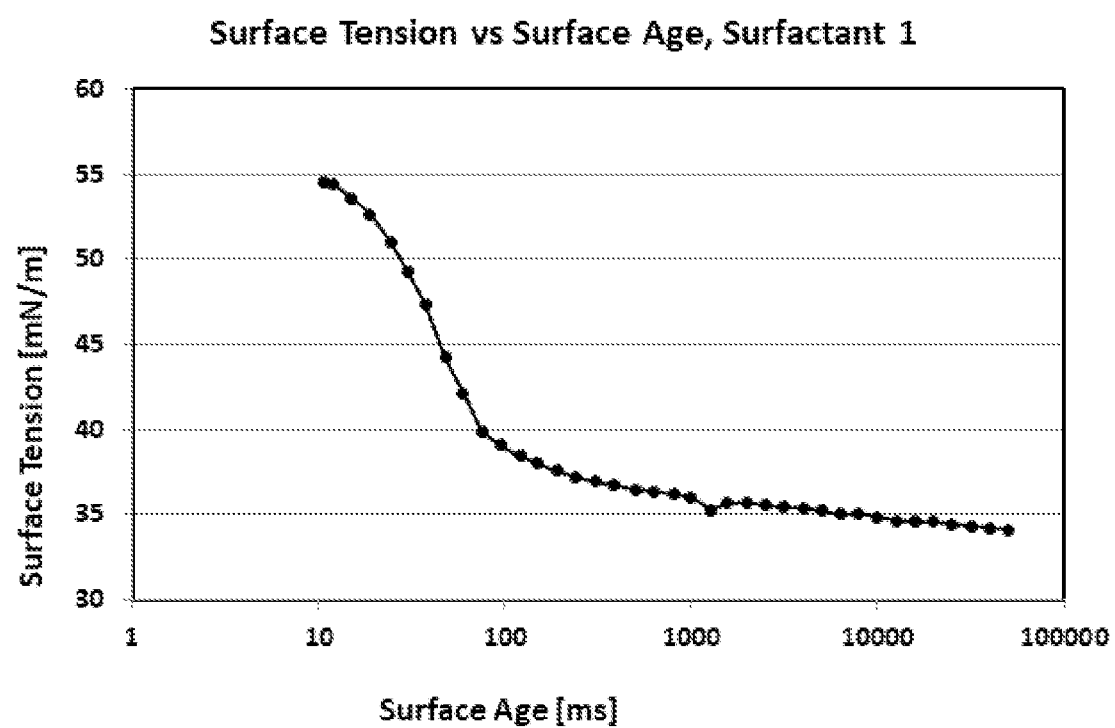
FIG. 2 shows a plot of dynamic surface tension as change in surface tension versus time for Surfactant 1 as described in Example 1c, wherein the Y axis depicts the surface tension in millinewtons per meter (mN/m) and the X axis depicts the surface age in milliseconds (ms).

The dynamic surface tension was determined with a bubble pressure tensiometer which measures the change of surface tension of a freshly created air-water interface with time. FIG. 2 present a plot of the results as surface tension versus time, showing that surface tension in the time interval between 1 ms and 75 ms drops rapidly from about 55.5 mN/m to about 39.9 mN/m. In the time interval between 75 ms and 50,410 ms, the surface tension drops slowly from about 39.9 mN/m to about 34 mN/m, approaching asymptotically the saturation value of the surface tension at the CMC.

Example 1d

Determination of Wetting Properties of Surfactant 1

In addition to surface tension and surface dynamics, the wetting properties of the compound were tested on various surfaces. For example, hydrophobic substrates such as polyethylene-HD exhibit surface wetting with a contact angle of 32°. On oleophobic and hydrophobic substrates such as Teflon, the measured contact angle was much less than that of water, 67.1° (Table 2).

TABLE 2

| Substrate | CA of Surfactant (°) | Concentration | CA of water (°) |
| --- | --- | --- | --- |
| Teflon | 67.1 | 10 × CMC | 119 |
| Polyethylene-HD | 32 | 10 × CMC | 93.6 |
| Nylon | 31.5 | 10 × CMC | 50 |
| Polyethylene terephthalate | 38.4 | 10 × CMC | 65.3 |

Example 2a

Synthesis of dodecyl 6-(dimethylamino)hexanoate N-oxide (Surfactant 2)

6-(Dimethylamino)hexanoic acid (11.99 g, 75.36 mmol) was dissolved in toluene (50 mL) in a round bottom flask equipped with a Dean-Stark trap. Dodecanol (12.68 g, 75.36 mmol) and p-toluene sulfonic acid monohydrate (PTSA) (14.33 g, 75.36 mmol) were then added. The reaction was heated to reflux for 24 hours, until no further water was noted in the Dean-Stark trap. The solvent was removed under vacuum and the resultant solid was washed with hexanes. The solid was dissolved in dichloromethane (200 mL) and washed with saturated sodium carbonate to give dodecyl 6-(dimethylamino)hexanoate in 51% yield. $^1$H NMR (DMSO) δ 4.00 (t, J=6.5 Hz, 2H), 2.27 (t, J=7.3 Hz, 2H), 2.13-2.16 (m, 2H), 2.01 (s, 6H), 1.54-1.53 (m, 6H), 1.27-1.18 (m, 20H), 0.86 (t, 3H).

Dodecyl 6-(dimethylamino)hexanoate (1.0 g, 3.05 mmol) was dissolved in distilled water (80 mL). Hydrogen peroxide (50% solution, 1.04 g, 30.5 mmol) was added. The reaction was heated at reflux for 12 hours, then the solvent was removed under vacuum. The resultant solid was washed with acetone to give the desired N-oxide in 90% yield. $^1$H NMR (500 MHz, DMSO) δ 4.00 (t, J=6.6 Hz, 2H), 3.30-3.26 (m, 2H), 3.18 (s, 6H), 2.31 (t, J=7.4 Hz, 2H), 1.76-1.73 (m, 2H), 1.54-1.57 (m, 4H), 1.30-1.24 (m, 22H), 0.86 (t, J=6.9 Hz, 3H).

Example 2b

Determination of Critical Micelle Concentration (CMC) of Surfactant 2

Figure 3:
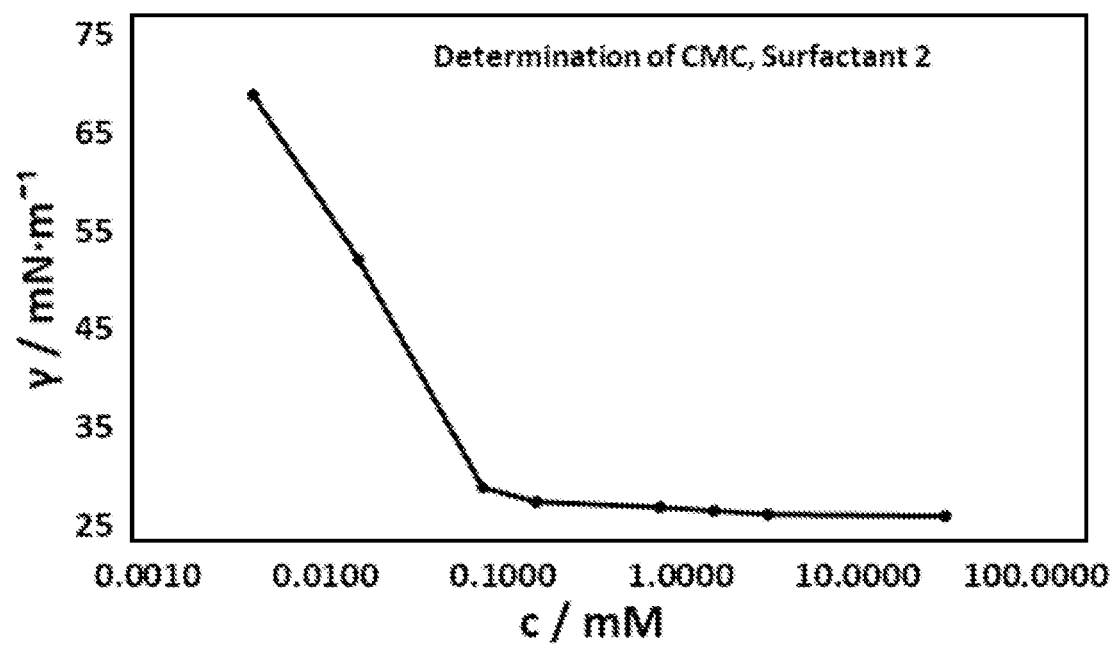
FIG. 3 shows a plot of surface tension versus concentration for Surfactant 2 measured at pH=7 as described in Example 2b, wherein the Y axis depicts the surface tension ($\gamma$) in millinewtons per meter (mN/m) and the X axis depicts the concentration (c) in millimoles (mM).

The critical micelle concentration (CMC) was tested. From the change in surface tension with concentration in water, the CMC was determined to be about 0.08 mmol. The plateau value of minimum surface tension that can be reached by this surfactant is about 28 mN/m, namely 28 mN/m±2.8 mN/m. FIG. 3 is a plot of these results, showing surface tension versus concentration. From the plot of the results, the surface tension at the CMC is equal to or less than about 30 mN/m. The plot further shows surface tension of equal to or less than 30 mN/m at a concentration of 0.08 mmol or greater.

Example 2c

Determination of Dynamic Surface Tension of Surfactant 2

Figure 4:
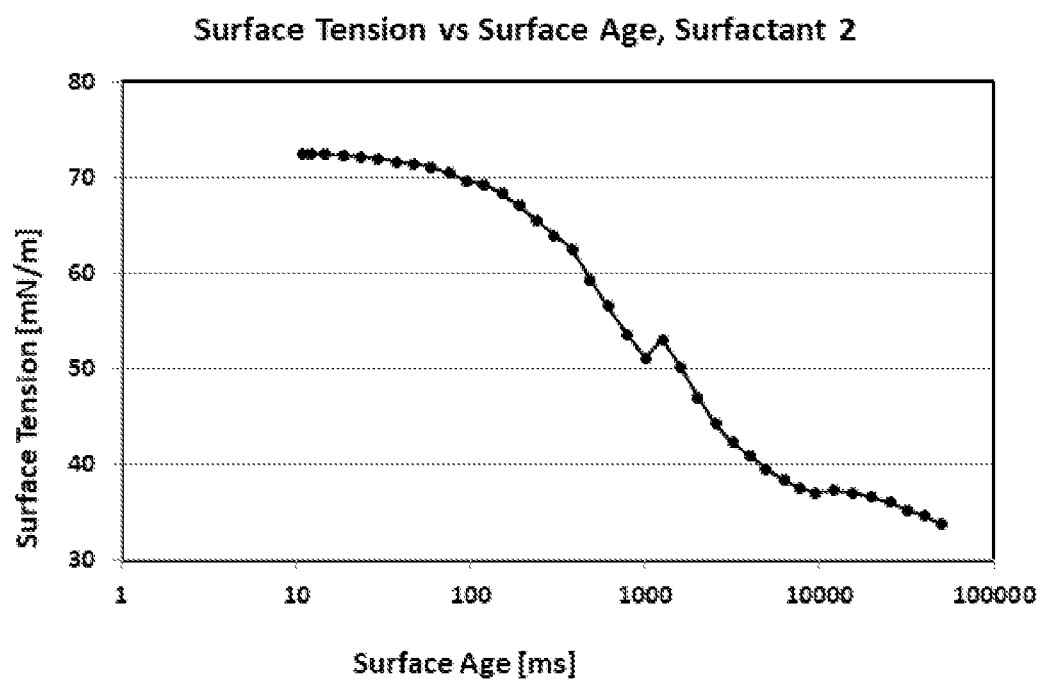
FIG. 4 shows a plot of dynamic surface tension as change in surface tension versus time for Surfactant 2 as described in Example 2c, wherein the Y axis depicts the surface tension in millinewtons per meter (mN/m) and the X axis depicts the surface age in milliseconds (ms).

The dynamic surface tension was determined with a bubble pressure tensiometer which measures the change of surface tension of a freshly created air-water interface with time. FIG. 4 presents a plot of the surface tension versus time, showing that the compound fully saturated the surface in approximately 7.6 seconds. As can be seen in the plot, the dynamic surface tension is equal to or less than 40 mN/m at a surface age of 4900 ms or greater.

Example 2d

Determination of Wetting Properties of Surfactant 2

In addition to surface tension and surface dynamics, the wetting properties of the compound were tested on various surfaces. For example, hydrophobic substrates such as polyethylene-HD exhibit surface wetting with a contact angle of 39.3°, much lower than that of water. On oleophobic and hydrophobic substrates such as Teflon, the measured contact angle was much less than that of water, 57.4° (Table 3).

TABLE 3

| Substrate | CA of Surfactant (°) | Concentration | CA of water (°) |
| --- | --- | --- | --- |
| Teflon | 57.4 | 10 × CMC | 119 |
| Polyethylene-HD | 39.3 | 10 × CMC | 93.6 |
| Nylon | 21.7 | 10 × CMC | 50 |
| Polyethylene terephthalate | 24.5 | 10 × CMC | 65.3 |

Example 3a

Synthesis of 6-(dodecyloxy)-N,N-dimethyl-6-oxo-hexan-1-aminium chloride (Surfactant 3)

6-(Dimethylamino)hexanoic acid (11.99 g, 75.36 mmol) was dissolved in toluene (50 mL) in a round bottom flask equipped with a Dean-Stark trap. Dodecanol (12.68 g, 75.36 mmol) and p-toluene sulfonic acid monohydrate (PTSA)

(14.33 g, 75.36 mmol) were then added. The reaction was heated to reflux for 24 hours, until no further water was noted in the Dean-Stark trap. The solvent was removed under vacuum and the resultant solid was washed with hexanes. The solid was dissolved in dichloromethane (200 mL) and washed with saturated sodium carbonate to give dodecyl 6-(dimethylamino)hexanoate in 51% yield. $^1$H NMR (DMSO) δ 4.00 (t, J=6.5 Hz, 2H), 2.27 (t, J=7.3 Hz, 2H), 2.13-2.16 (m, 2H), 2.01 (s, 6H), 1.54-1.53 (m, 6H), 1.27-1.18 (m, 20H), 0.86 (t, 3H).

Dodecyl 6-(dimethylamino)hexanoate (100 mg, 0.305 mmol) was dissolved in water (10 mL). Concentrated hydrochloric acid (11.14 mg, 0.305 mmol) was added.

Example 3b

Determination of Critical Micelle Concentration (CMC) of Surfactant 3

Figure 5:
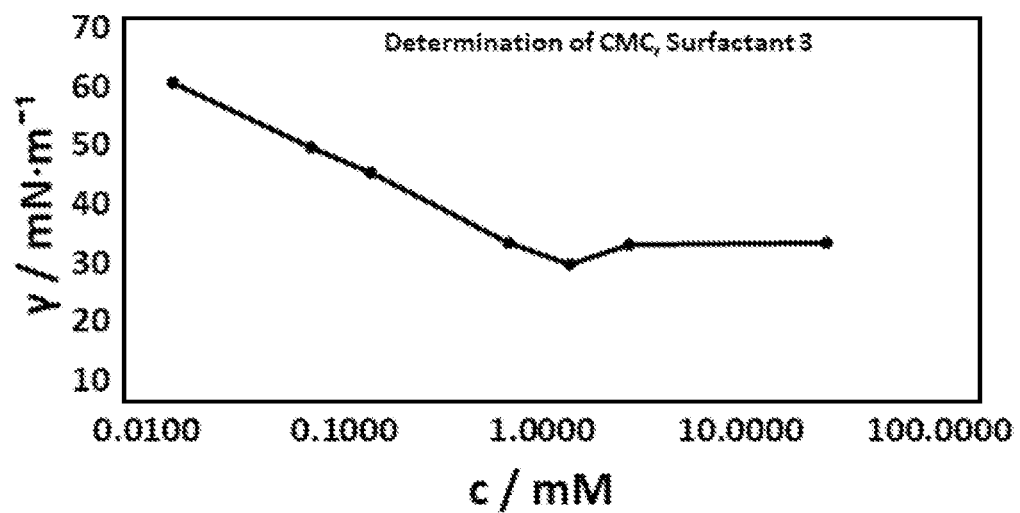
FIG. 5 shows a plot of surface tension versus concentration for Surfactant 3 measured at pH=7 as described in Example 3b, wherein the Y axis depicts the surface tension ($\gamma$) in millinewtons per meter (mN/m) and the X axis depicts the concentration (c) in millimoles (mM).

The critical micelle concentration (CMC) was tested. From the change in surface tension with concentration in water, the CMC was determined to be about 1.4 mmol. The plateau value of minimum surface tension that can be reached by this surfactant is about 30 mN/m, namely 30 mN/m±3 mN/m. FIG. 5 is a plot of these results, showing surface tension versus concentration. From the plot of the results, the surface tension at the CMC is equal to or less than about 30 mN/m. The plot further shows the surface tension to be equal to or less than 33 mN/m at a concentration of 2.7 mmol or greater.

Example 3c

Determination of Dynamic Surface Tension of Surfactant 3

Figure 6:
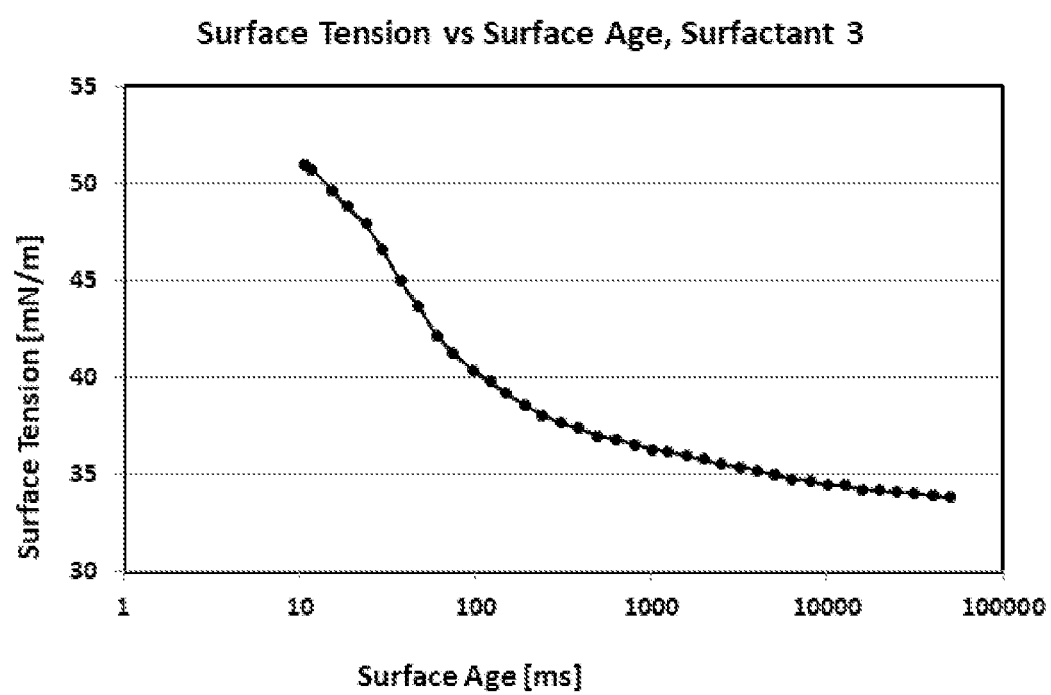
FIG. 6 shows a plot of dynamic surface tension as change in surface tension versus time for Surfactant 3 as described in Example 3c, wherein the Y axis depicts the surface tension in millinewtons per meter (mN/m) and the X axis depicts the surface age in milliseconds (ms).

The dynamic surface tension was determined with a bubble pressure tensiometer which measures the change of surface tension of a freshly created air-water interface with time. FIG. 6 presents a plot of the surface tension versus time, showing that surface tension in the time interval between 1 and 100 ms drops rapidly from about 50 mN/m to about 40 mN/m. In the time interval from 100 to 50,000 ms, the surface tension drops slowly from 40 mN/m to about 34 mN/m, approaching asymptotically the saturation value of the surface tension at the CMC.

Example 3d

Determination of Wetting Properties of Surfactant 3

In addition to surface tension and surface dynamics, the wetting properties of the compound were tested on various surfaces. For example, hydrophobic substrates such as polyethylene-HD exhibit surface wetting with a contact angle of 42.5°. On oleophobic and hydrophobic substrates such as Teflon, the measured contact angle was much less than that of water, 66.6° (Table 4).

TABLE 4

| Substrate | CA of Surfactant (°) | Concentration | CA of water (°) |
|---|---|---|---|
| Teflon | 66.6 | 10 × CMC | 119 |
| Polyethylene-HD | 42.5 | 10 × CMC | 93.6 |

TABLE 4-continued

| Substrate | CA of Surfactant (°) | Concentration | CA of water (°) |
|---|---|---|---|
| Nylon | 15 | 10 × CMC | 50 |
| Polyethylene terephthalate | 18.3 | 10 × CMC | 65.3 |

Example 4a

Synthesis of 4-((6-(dodecyloxy)-6-oxohexyl)dimethylammonio)butane-1-sulfonate (Surfactant 4)

6-(Dimethylamino)hexanoic acid (11.99 g, 75.36 mmol) was dissolved in toluene (50 mL) in a round bottom flask equipped with a Dean-Stark trap. Dodecanol (12.68 g, 75.36 mmol) and p-toluene sulfonic acid monohydrate (PTSA) (14.33 g, 75.36 mmol) were then added. The reaction was heated to reflux for 24 hours, until no further water was noted in the Dean-Stark trap. The solvent was removed under vacuum and the resultant solid was washed with hexanes. The solid was dissolved in dichloromethane (200 mL) and washed with saturated sodium carbonate to give dodecyl 6-(dimethylamino)hexanoate in 51% yield. 1H NMR (DMSO) δ 4.00 (t, J=6.5 Hz, 2H), 2.27 (t, J=7.3 Hz, 2H), 2.13-2.16 (m, 2H), 2.01 (s, 6H), 1.54-1.53 (m, 6H), 1.27-1.18 (m, 20H), 0.86 (t, 3H).

Dodecyl 6-(dimethylamino)hexanoate (1.0 g, 3.05 mmol) was dissolved in ethyl acetate (30 mL). 1,4-Butanesultone (0.62 g, 4.57 mmol) was then added, and the mixture was heated to reflux for 12 hours. The reaction was cooled to room temperature, and the solvent was removed under vacuum. 1H NMR (DMSO) δ 4.00 (t, J=6.7 Hz, 2H), 3.29-3.15 (m, 4H), 2.97 (s, 6H), 2.47 (t, J=7.4 Hz, 2H), 2.33 (t, J=7.4 Hz, 2H), 1.81-1.70 (m, 2H), 1.66-1.55 (m, 6H), 1.32-1.23 (m, 20H), 0.86 (t, J=6.9 Hz, 3H).

Example 4b

Determination of Critical Micelle Concentration (CMC) of Surfactant 4

Figure 7:
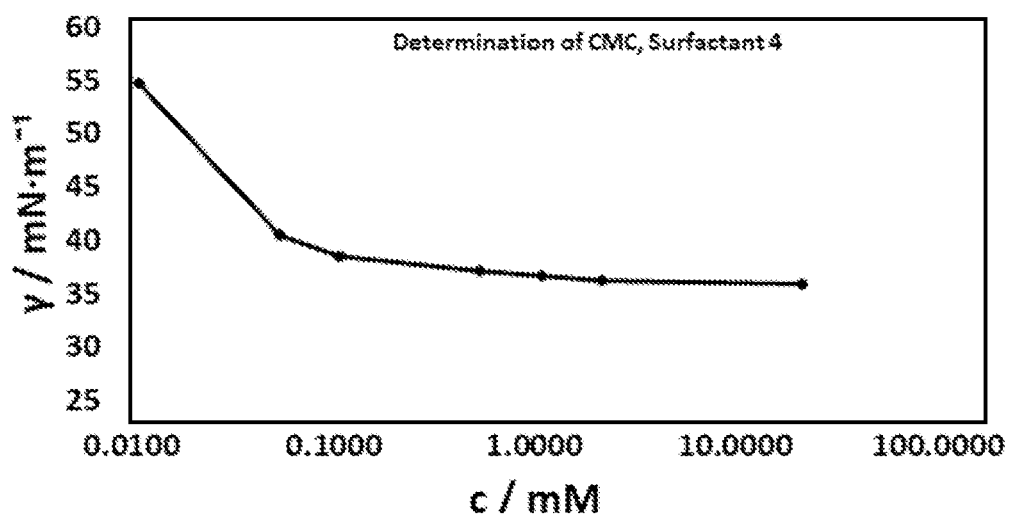
FIG. 7 shows a plot of surface tension versus concentration for Surfactant 4 measured at pH=7 as described in Example 4b, wherein the Y axis depicts the surface tension ($\gamma$) in millinewtons per meter (mN/m) and the X axis depicts the concentration (c) in millimoles (mM).

The critical micelle concentration (CMC) was tested. From the change in surface tension with concentration in water, the CMC was determined to be about 0.1 mmol. The plateau value of minimum surface tension that can be reached by this surfactant is about 38 mN/m, namely 38 mN/m±3.8 mN/m. FIG. 7 is a plot of these results, showing surface tension versus concentration. From the plot of the results, the surface tension at the CMC is about 38 mN/m, and the surface tension is equal to or less than 37 mN/m at a concentration of 1 mmol or greater.

Example 4c

Determination of Dynamic Surface Tension of Surfactant 4

Figure 8:
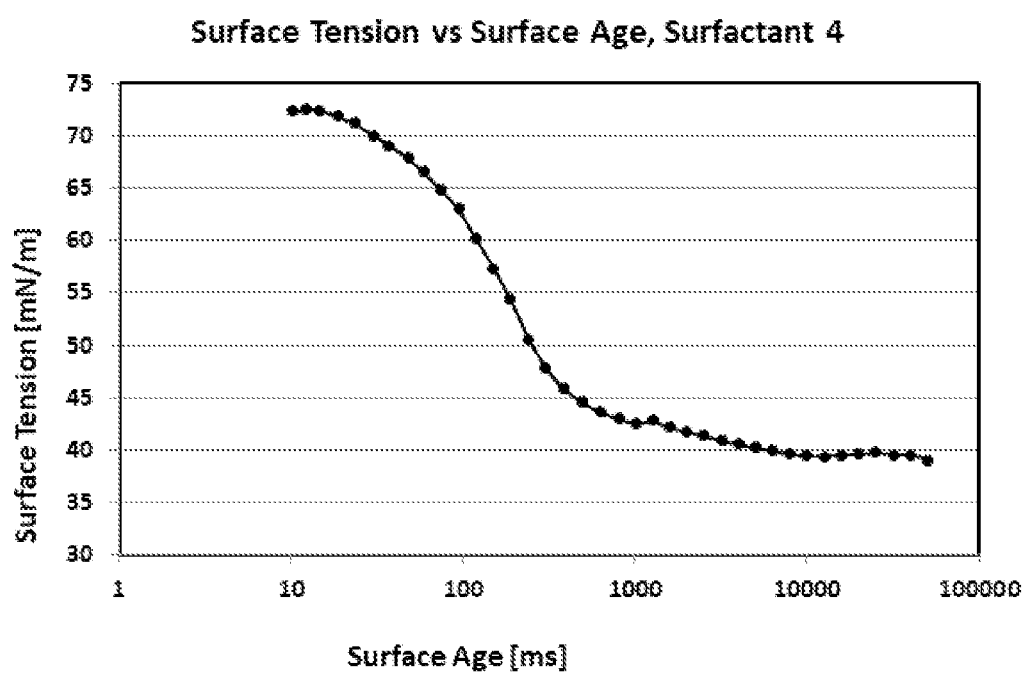
FIG. 8 shows a plot of dynamic surface tension as change in surface tension versus time for Surfactant 4 as described in Example 4c, wherein the Y axis depicts the surface tension in millinewtons per meter (mN/m) and the X axis depicts the surface age in milliseconds (ms).

The dynamic surface tension was determined with a bubble pressure tensiometer which measures the change of surface tension of a freshly created air-water interface with time. FIG. 8 presents a plot of the surface tension versus time, showing that the compound fully saturated the surface in approximately 1 second. From the plot, the dynamic surface tension is equal to or less than 40.5 mN/m at a surface age of 4000 ms or greater.

Example 4d

Determination of Wetting Properties of Surfactant 4

In addition to surface tension and surface dynamics, the wetting properties of the compound were tested on various surfaces. For example, hydrophobic substrates such as polyethylene-HD exhibit surface wetting with a contact angle of 46.5°. On oleophobic and hydrophobic substrates such as Teflon, the measured contact angle was much less than that of water, 62.7° (Table 5).

TABLE 5

| Substrate | CA of Surfactant (°) | Concentration | CA of water (°) |
|---|---|---|---|
| Teflon | 62.7 | 10 × CMC | 119 |
| Polyethylene-HD | 46.5 | 10 × CMC | 93.6 |
| Nylon | 25.7 | 10 × CMC | 50 |
| Polyethylene terephthalate | 35.6 | 10 × CMC | 65.3 |

Example 5a

Synthesis of 6-(dodecyloxy)-6-oxohexan-1-aminium chloride (Surfactant 5)

6-Aminohexanoic acid (5.0 g, 38.11 mmol) was dissolved in toluene (50 mL) in a round bottom flask equipped with a Dean-Stark trap. Dodecanol (6.41 g, 38.11 mmol) and p-toluene sulfonic acid monohydrate (PTSA) (7.24 g, 38.11 mmol) were then added. The reaction was heated to reflux for 24 hours, until no further water was noted in the Dean-Stark trap. The solvent was removed under vacuum and the resultant solid was washed with hexanes. The solid was dissolved in dichloromethane (200 mL) and washed with saturated sodium carbonate to give dodecyl 6-aminohexanoate in 40% yield.

Dodecyl 6-aminohexanoate (100 mg, 0.363 mmol) was dissolved in water (10 mL). Concentrated hydrochloric acid (13.23 mg, 0.363 mmol) was then added.

Example 5b

Determination of Critical Micelle Concentration (CMC) of Surfactant 5

Figure 9:
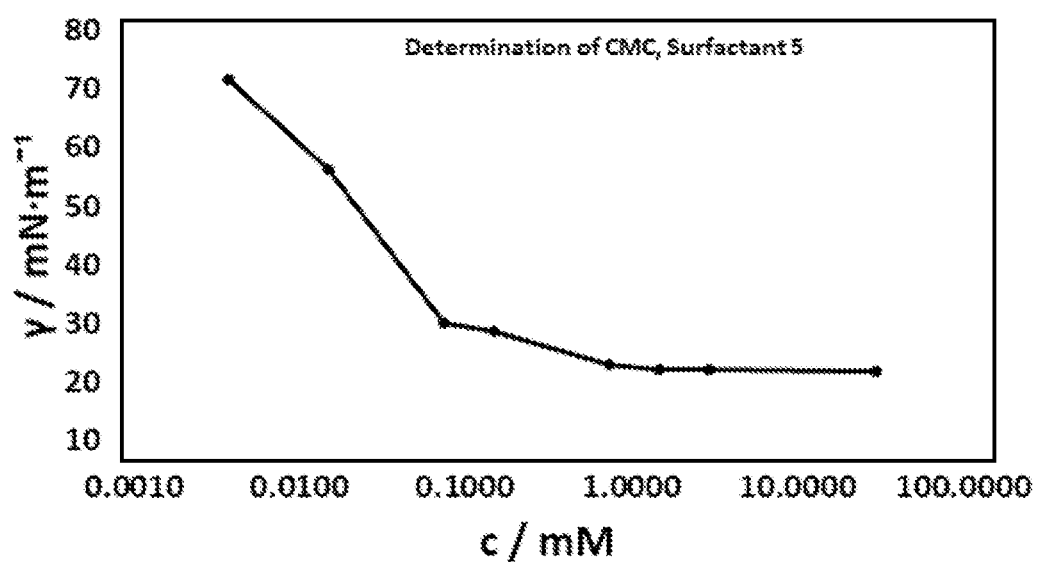
FIG. 9 shows a plot of surface tension versus concentration for Surfactant 5 measured at pH=7 as described in Example 5b, wherein the Y axis depicts the surface tension ($\gamma$) in millinewtons per meter (mN/m) and the X axis depicts the concentration (c) in millimoles (mM).

The critical micelle concentration (CMC) was tested. From the change in surface tension with concentration in water, the CMC was determined to be about 0.75 mmol. The plateau value of minimum surface tension that can be reached by this surfactant is about 23 mN/m, namely 23 mN/m±2.3 mN/m. FIG. 9 is a plot of these results, showing surface tension versus concentration. From the plot of the results, the surface tension at the CMC is about 23 mN/m, and surface tension is equal to or less than 23.2 mN/m at a concentration of 0.7 mmol or greater.

Example 5c

Determination of Dynamic Surface Tension of Surfactant 5

Figure 10:
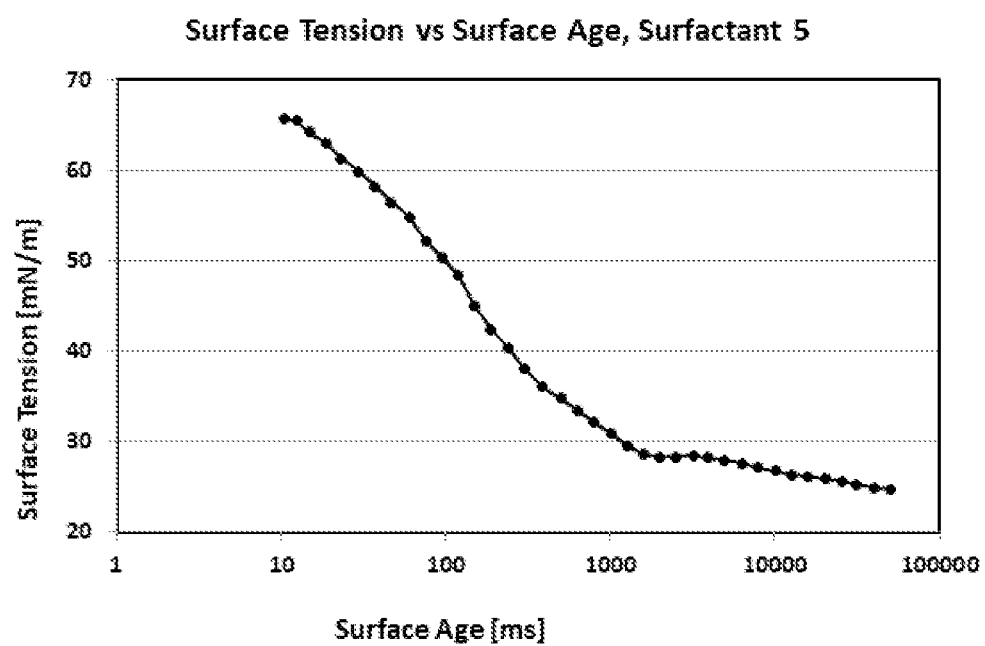
FIG. 10 shows a plot of dynamic surface tension as change in surface tension versus time for Surfactant 5 as described in Example 5c, wherein the Y axis depicts the surface tension in millinewtons per meter (mN/m) and the X axis depicts the surface age in milliseconds (ms).

The dynamic surface tension was determined with a bubble pressure tensiometer which measures the change of surface tension of a freshly created air-water interface with time. FIG. 10 shows a plot of the results as surface tension versus time, showing that the compound fully saturated the surface in approximately 1.5 seconds. From the plot, the dynamic surface tension is equal to or less than 28.5 mN/m at a surface age of 3185 ms or greater.

Example 5d

Determination of Wetting Properties of Surfactant 5

In addition to surface tension and surface dynamics, the wetting properties of the compound were tested on various surfaces. For example, hydrophobic substrates such as polyethylene-HD exhibit surface wetting with a very low contact angle of 16.6°. On oleophobic and hydrophobic substrates such as Teflon, the measured contact angle was much less than that of water, 39.3° (Table 6).

TABLE 6

| Substrate | CA of Surfactant (°) | Concentration | CA of water (°) |
|---|---|---|---|
| Teflon | 39.3 | 10 × CMC | 119 |
| Polyethylene-HD | 16.6 | 10 × CMC | 93.6 |
| Nylon | 18.2 | 10 × CMC | 50 |
| Polyethylene terephthalate | 15.3 | 10 × CMC | 65.3 |

Example 6

Formulation for Pesticides

In this Example, a concentrated formulation for use as a pesticide is provided, including a surfactant, which may be one or more of Surfactants 1-5 described herein. The components of the formulation are shown below in Table 7. The formulation may also include additional surfactants, water, thickeners, deposition enhancers, drift control agents, and salts.

TABLE 7

| Component | Function | Weight % |
|---|---|---|
| Pesticide | Agriculturally Active Agent | 5-40 |
| Surfactant | Emulsifier | 20-80 |
| Water-Insoluble Solvent | Solvent | 0.1-50 |

Example 7

Formulation for Liquid Fungicidal Composition

In this Example, a formulation for use as liquid fungicidal composition is provided, including a surfactant, which may be one or more of Surfactants 1-5 described herein. The formulation is shown below in Table 8.

TABLE 8

| Component | Function | Weight % |
|---|---|---|
| Fungicide | Agriculturally Active Agent | 1-90 |
| Surfactant | Emulsifier | 1-30 |
| Co-Surfactant | Co-Emulsifier | 0-20 |
| Water-Insoluble Solvent | Solvent | 0-90 |

Example 8

Formulation for Herbicide

In this Example, a formulation for use as an herbicide is provided, including a surfactant, which may be one or more of Surfactants 1-5 described herein. The formulation is shown below in Table 9.

TABLE 9

| Component | Function | Weight % |
|---|---|---|
| Herbicide Salt | Agriculturally Active Agent | 5-70 |
| Second Herbicide | Agriculturally Active Agent | 0.1-40 |
| Surfactant | Emulsifier | 0-15 |
| Water-Insoluble Solvent | Solvent | 0-50 |
| Water | | 20-80 |

Example 9

Formulation for Insecticide

In this Example, a formulation for use as an insecticide is provided, including a surfactant, which may be one or more of Surfactants 1-5 described herein. The formulation is shown below in Table 10.

TABLE 10

| Component | Function | Weight % |
|---|---|---|
| Insecticide | Agriculturally Active Agent | 5-70 |
| Surfactant | | 0.1-40 |
| Surfactant | Antifoaming Agent | 0-15 |
| Thickener | Viscosity Modifier | 0-50 |
| Water | | 20-80 |

ASPECTS

Aspect 1 is a formulation for a pesticide, comprising: at least one surfactant of Formula I,

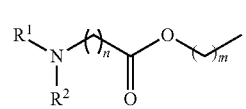

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide; and a pesticide.

Aspect 2 is the formulation of Aspect 1, further comprising a water-insoluble solvent.

Aspect 3 is the formulation according to either Aspect 1 or Aspect 2, wherein the surfactant is 6-(dodecyloxy)-N,N,N-trimethyl-6-oxohexan-1-aminium iodide, having the following formula:

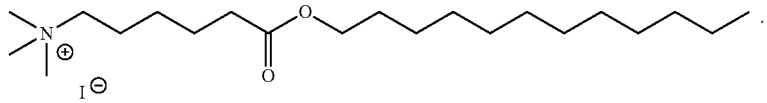 [SMILES: CCCCCCCCCCCCOC(=O)CCCCC[N+](C)(C)C ; [I-]]

Aspect 4 is the formulation according to either Aspect 1 or Aspect 2, wherein the surfactant is dodecyl 6-(dimethylamino)hexanoate N-oxide, having the following formula:

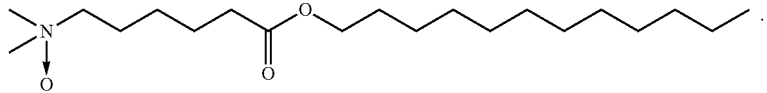 [SMILES: CCCCCCCCCCCCOC(=O)CCCCC[N+](C)(C)[O-]]

Aspect 5 is the formulation according to either Aspect 1 or Aspect 2, wherein the surfactant is 6-(dodecyloxy)-N,N-dimethyl-6-oxohexan-1-aminium chloride, having the following formula:

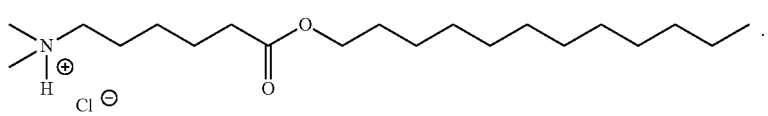 [SMILES: CCCCCCCCCCCCOC(=O)CCCCC[NH+](C)C ; [Cl-]]

Aspect 6 is the formulation according to either Aspect 1 or Aspect 2, wherein the surfactant is 4-((6-(dodecyloxy)-6-oxohexyl)dimethylammonio)butane-1-sulfonate, having the following formula:

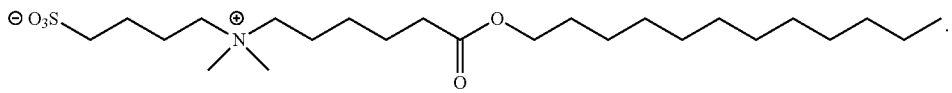

Aspect 7 is the formulation according to either Aspect 1 or Aspect 2, wherein the surfactant is 6-(dodecyloxy)-6-oxohexan-1-aminium chloride, having the following formula:

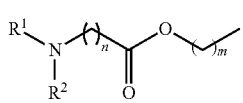 

Aspect 8 is a formulation for a fungicide, comprising: Formula I,

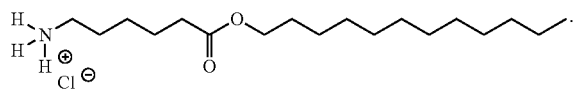

wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide; and a fungicide.

Aspect 9 is the formulation of Aspect 8, further comprising a co-surfactant.

Aspect 10 is the formulation of either of Aspect 8 or Aspect 9, further comprising a carrier agent.

Aspect 11 is the formulation according to any of Aspects 8-10, wherein the surfactant is 6-(dodecyloxy)-N,N,N-trimethyl-6-oxohexan-1-aminium iodide, having the following formula:

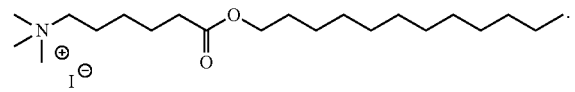

Aspect 12 is the formulation according to any of Aspects 8-10, wherein the surfactant is dodecyl 6-(dimethylamino) hexanoate N-oxide, having the following formula:

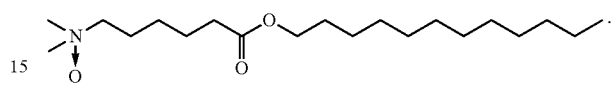

Aspect 13 is the formulation according to any of Aspects 8-10, wherein the surfactant is 6-(dodecyloxy)-N,N-dimethyl-6-oxohexan-1-aminium chloride, having the following formula:

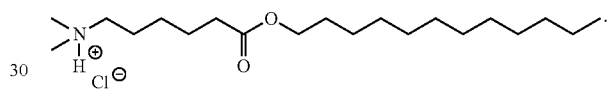

Aspect 14 is the formulation according to any of Aspects 8-10, wherein the surfactant is 4-((6-(dodecyloxy)-6-oxohexyl)dimethylammonio)butane-1-sulfonate, having the following formula:

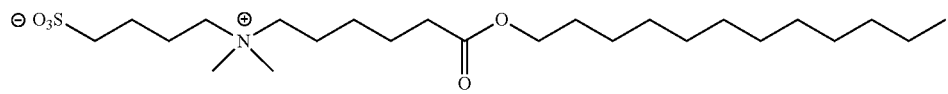

Aspect 15 is the formulation according to any of Aspects 8-10, wherein the surfactant is 6-(dodecyloxy)-6-oxohexan-1-aminium chloride, having the following formula:

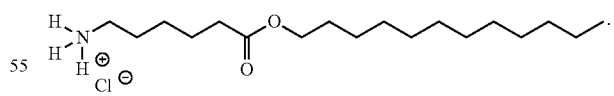

Aspect 16 is a formulation for an herbicide, comprising: at least one surfactant of Formula I, Formula I

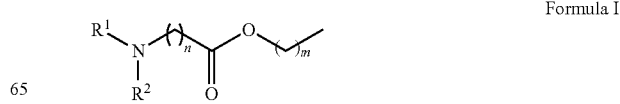

wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide; and an herbicide.

Aspect 17 is the formulation of Aspect 16, further comprising a second herbicide.

Aspect 18 is the formulation of either Aspect 16 or Aspect 17, further comprising a water-insoluble solvent.

Aspect 19 is the formulation of any of Aspects 16-18, further comprising water.

Aspect 20 is the formulation according to any of Aspects 16-19, wherein the surfactant is 6-(dodecyloxy)-N,N,N-trimethyl-6-oxohexan-1-aminium iodide, having the following formula:

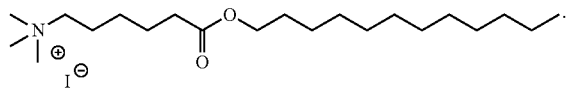

Aspect 21 is the formulation according to any of Aspects 16-19, wherein the surfactant is dodecyl 6-(dimethylamino) hexanoate N-oxide, having the following formula:

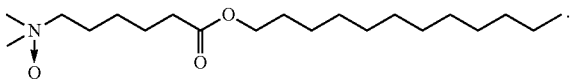 [SMILES: CCCCCCCCCCCCOC(=O)CCCCC[N+](C)(C)[O-]]

Aspect 22 is the formulation according to any of Aspects 16-19, wherein the surfactant is 6-(dodecyloxy)-N,N-dimethyl-6-oxohexan-1-aminium chloride, having the following formula:

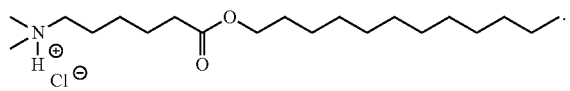

Aspect 23 is the formulation according to any of Aspects 16-19, wherein the surfactant is 4-((6-(dodecyloxy)-6-oxohexyl)dimethylammonio)butane-1-sulfonate, having the following formula:

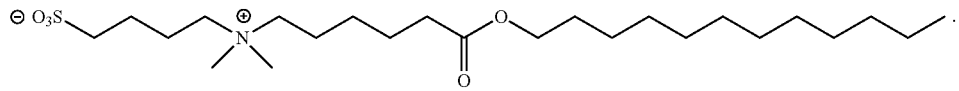

Aspect 24 is the formulation according to any of Aspects 16-19, wherein the surfactant is 6-(dodecyloxy)-6-oxohexan-1-aminium chloride, having the following formula:

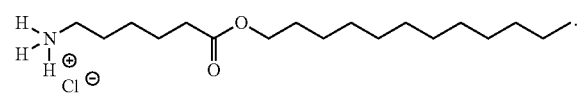

Aspect 25 is a formulation for an insecticide, comprising: at least one surfactant of Formula I,

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; n is an integer from 2 to 5 (including 2 and 5); m is an integer from 9 to 20 (including 9 and 20); the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate; an optional counterion associated with the compound which, if present, is selected from the group consisting of chloride, bromide, iodide, and hydroxide; and an insecticide.

Aspect 26 is the formulation of Aspect 25, further comprising an antifoaming agent.

Aspect 27 is the formulation of either of Aspect 25 or Aspect 26, further comprising an antifreezing agent.

Aspect 28 is the formulation of any of Aspects 25-27, further comprising water.

Aspect 29 is the formulation of any of Aspects 25-27, wherein the surfactant is 6-(dodecyloxy)-N,N,N-trimethyl-6-oxohexan-1-aminium iodide, having the following formula:

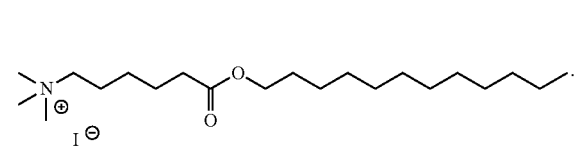 [SMILES: CCCCCCCCCCCCOC(=O)CCCCC[N+](C)(C)C ; [I-]]

Aspect 30 is the formulation of any of Aspects 25-27, wherein the surfactant is dodecyl 6-(dimethylamino)hexanoate N-oxide, having the following formula:

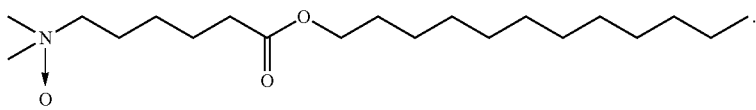

Aspect 31 is the formulation of any of Aspects 25-27, wherein the surfactant is 6-(dodecyloxy)-N,N-dimethyl-6-oxohexan-1-aminium chloride, having the following formula:

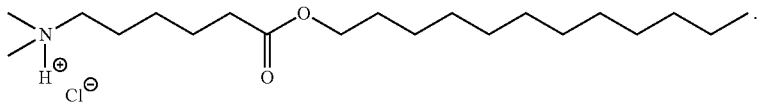

Aspect 32 is the formulation of any of Aspects 25-27, wherein the surfactant is 4-((6-(dodecyloxy)-6-oxohexyl)dimethylammonio)butane-1-sulfonate, having the following formula:

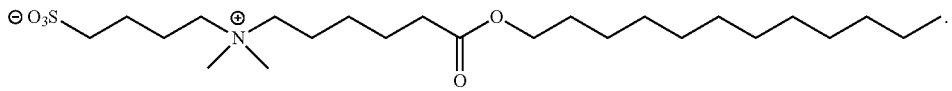

Aspect 33 is the formulation of any of Aspects 25-27, wherein the surfactant is 6-(dodecyloxy)-6-oxohexan-1-aminium chloride, having the following formula:

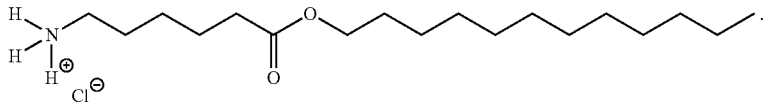

Aspect 34 is the formulation of either Aspect 1 or Aspect 2, wherein the pesticide is an insecticide.

Aspect 35 is the formulation of Aspect 34, further comprising an antifoaming agent.

Aspect 36 is the formulation of either Aspect 34 or Aspect 35, further comprising an antifreezing agent.

Aspect 37 is the formulation of any of Aspects 34-36, further comprising water.

Aspect 38 is the formulation of any of Aspect 1, Aspect 2, or Aspects 34-37, wherein the surfactant comprises at least one of 6-(dodecyloxy)-N,N,N-trimethyl-6-oxohexan-1-aminium iodide, having the following formula:

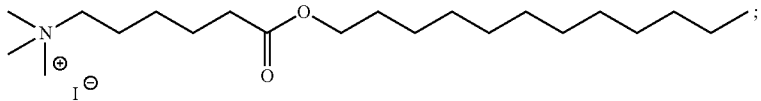

dodecyl 6-(dimethylamino)hexanoate N-oxide, having the following formula:

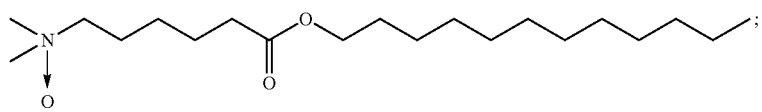

6-(dodecyloxy)-N,N-dimethyl-6-oxohexan-1-aminium chloride, having the following formula:

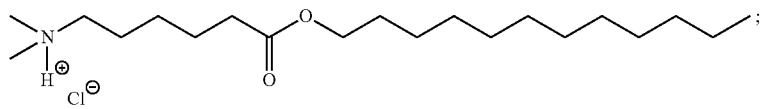

4-((6-(dodecyloxy)-6-oxohexyl)dimethylammonio)butane-1-sulfonate, having the following formula:

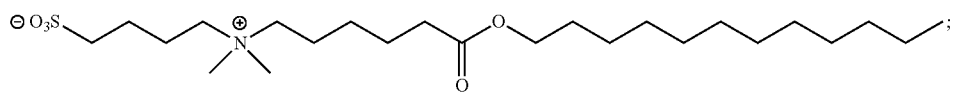

6-(dodecyloxy)-6-oxohexan-1-aminium chloride, having the following formula:

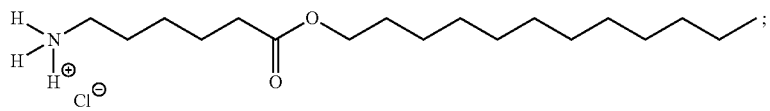

and combinations thereof.

Aspect 39 is the formulation of any of Aspects 8-10, wherein the surfactant comprises at least one of 6-(dodecyloxy)-N,N,N-trimethyl-6-oxohexan-1-aminium iodide, having the following formula:

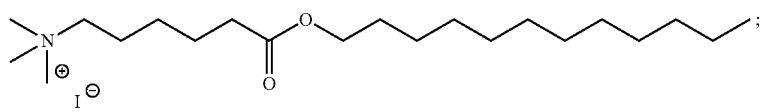

dodecyl 6-(dimethylamino)hexanoate N-oxide, having the following formula:

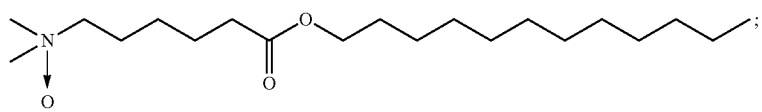

6-(dodecyloxy)-N,N-dimethyl-6-oxohexan-1-aminium chloride, having the following formula:

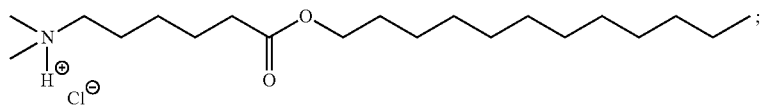

4-((6-(dodecyloxy)-6-oxohexyl)dimethylammonio)butane-1-sulfonate, having the following formula:

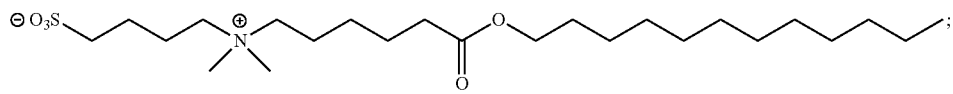

6-(dodecyloxy)-6-oxohexan-1-aminium chloride, having the following formula:

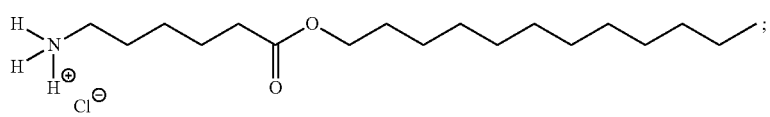

and combinations thereof.

Aspect 40 is the formulation of any of Aspects 16-19, wherein the surfactant comprises at least one of 6-(dodecyloxy)-N,N,N-trimethyl-6-oxohexan-1-aminium iodide, having the following formula:

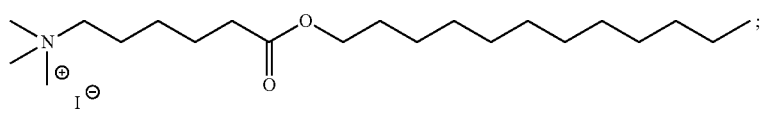

dodecyl 6-(dimethylamino)hexanoate N-oxide, having the following formula:

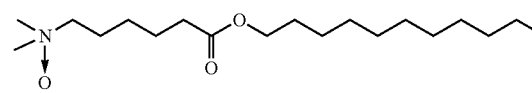

6-(dodecyloxy)-N,N-dimethyl-6-oxohexan-1-aminium chloride, having the following formula:

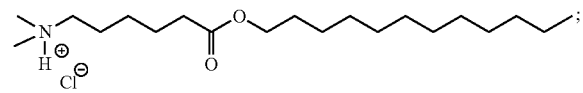

4-((6-(dodecyloxy)-6-oxohexyl)dimethylammonio)butane-1-sulfonate, having the following formula:

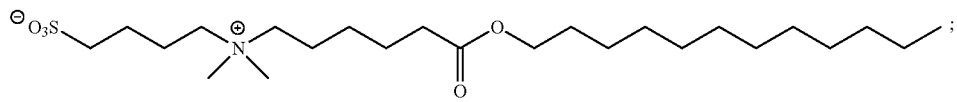

6-(dodecyloxy)-6-oxohexan-1-aminium chloride, having the following formula:

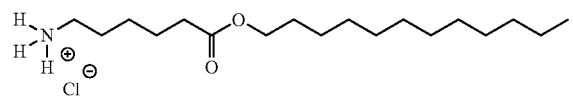

and combinations thereof.

The invention claimed is:
1. A formulation for a pesticide, comprising:
at least one surfactant of Formula I,

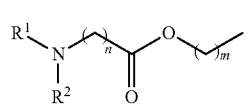

Formula I wherein $R^1$ and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate;

n is 5;

m is 11;

the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate;

an optional counterion associated with the compound which, if present, is hydroxide; and a pesticide.

2. The formulation of claim 1, further comprising a water-insoluble solvent.

3. The formulation of claim 1, wherein the surfactant comprises at least one of;

dodecyl 6-(dimethylamino)hexanoate N-oxide, having the following formula:

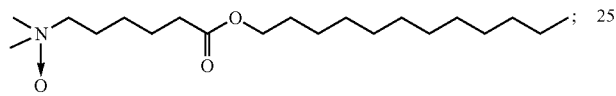

4-((6-(dodecyloxy)-6-oxohexyl)dimethylammonio)butane-1-sulfonate, having the following formula:

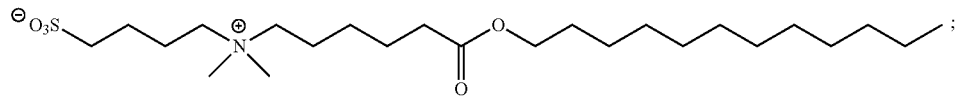

and combinations thereof.

4. The formulation of claim 1, wherein the pesticide is an insecticide.

5. The formulation of claim 4, further comprising an antifoaming agent.

6. The formulation of claim 4, further comprising an antifreezing agent.

7. The formulation of claim 4, further comprising water.

8. The formulation of claim 4, wherein the surfactant comprises at least one of;

dodecyl 6-(dimethylamino)hexanoate N-oxide, having the following formula:

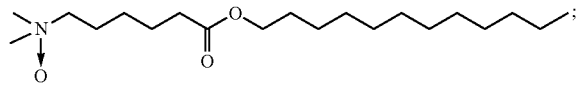

4-((6-(dodecyloxy)-6-oxohexyl)dimethylammonio)butane-1-sulfonate, having the following formula:

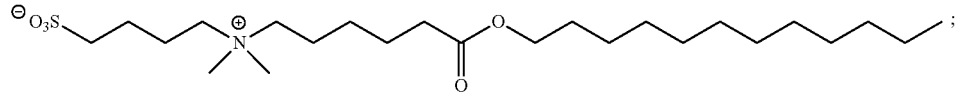

and combinations thereof.

9. A formulation for a fungicide, comprising:

at least one surfactant of Formula I,

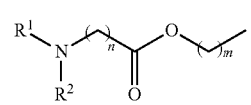

wherein R' and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate;

n is 5;

m is 11;

the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate;

an optional counterion associated with the compound which, if present, is hydroxide; and a fungicide.

10. The formulation of claim 9, further comprising a co-surfactant.

11. The formulation of claim 9, further comprising a carrier agent.

12. The formulation of claim 9, wherein the surfactant comprises at least one of;

dodecyl 6-(dimethylamino)hexanoate N-oxide, having the following formula:

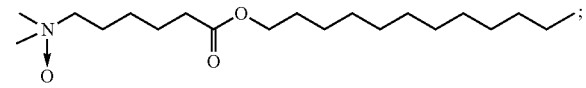

4-((6-(dodecyloxy)-6-oxohexyl)dimethylammonio)butane-1-sulfonate, having the following formula:

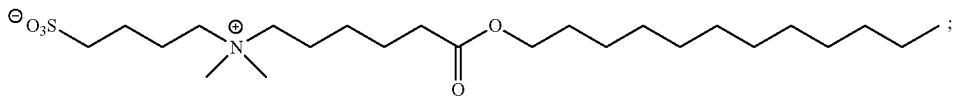

and combinations thereof.

13. A formulation for an herbicide, comprising:
at least one surfactant of Formula I,

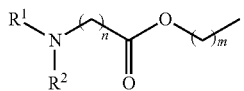

Formula I wherein R' and $R^2$ may be the same or different, and may be selected from the group consisting of hydrogen and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate;
n is 5;
m is 11;
the terminal nitrogen is optionally further substituted with $R^3$, wherein $R^3$ is selected from the group consisting of hydrogen, oxygen, hydroxyl, and $C_1$-$C_6$ alkyl, wherein the $C_1$-$C_6$ alkyl may optionally be substituted with one or more substituents selected from the group consisting of hydroxyl, amino, amido, sulfonyl, sulfonate, carbonyl, carboxyl, and carboxylate;
an optional counterion associated with the compound which, if present, is hydroxide; and
an herbicide.

14. The formulation of claim 13, further comprising a second herbicide.

15. The formulation of claim 13, further comprising a water-insoluble solvent.

16. The formulation of claim 13, further comprising water.

17. The formulation of claim 13, wherein the surfactant comprises at least one of;
dodecyl 6-(dimethylamino)hexanoate N-oxide, having the following formula:

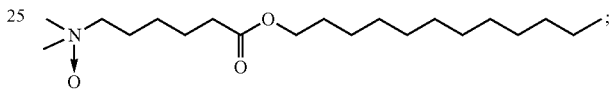

4-((6-(dodecyloxy)-6-oxohexyl)dimethylammonio)butane-1-sulfonate, having the following formula:

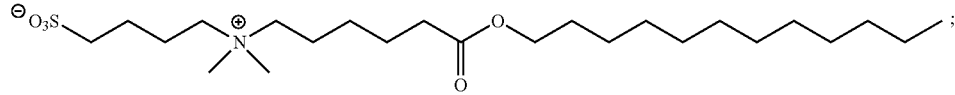

and combinations thereof.

* * * * *